US006902920B2

(12) United States Patent
Sobek et al.

(10) Patent No.: US 6,902,920 B2
(45) Date of Patent: Jun. 7, 2005

(54) METHOD FOR PRODUCING AN ACTIVE HETERODIMERIC AMV-RT IN PROKARYOTIC CELLS

(75) Inventors: Harald Sobek, Penzberg (DE); Rainer Mueller, Penzberg (DE); Manfred Schmidt, Penzberg (DE); Bruno Frey, Penzberg (DE); Bernhard Suppmann, Weilheim (DE); Rainer Schmuck, Benediktbeuern (DE); Johann-Peter Thalhofer, Weilheim (DE); Peter Pallua, Vienna (AT); Markus Pajatsch, Munich (DE)

(73) Assignee: Roche Diagnostics Operations, Inc., Indianaoplis, IN (US)

( * ) Notice: Subject to any disclaimer, the term of this patent is extended or adjusted under 35 U.S.C. 154(b) by 595 days.

(21) Appl. No.: 09/960,428

(22) Filed: Sep. 21, 2001

(65) Prior Publication Data

US 2002/0115147 A1 Aug. 22, 2002

(30) Foreign Application Priority Data

Sep. 22, 2000 (DE) .......................................... 100 46 960

(51) Int. Cl.⁷ ................................................. C12N 9/12
(52) U.S. Cl. ...................................................... 435/194
(58) Field of Search ................................ 435/194, 91.1

(56) References Cited

FOREIGN PATENT DOCUMENTS

| EP | 0688870 A1 | 12/1995 | ........... C12N/15/48 |
|---|---|---|---|
| EP | 0743365 A2 | 11/1996 | ........... C12N/15/67 |
| EP | 0774515 A2 | 5/1997 | ........... C12N/15/31 |
| EP | 0885967 A2 | 12/1998 | ........... C12N/15/70 |
| WO | WO98/07869 | 2/1998 | ........... C12N/15/52 |
| WO | WO 98/47912 | 10/1998 | ............ C07K/1/00 |
| WO | WO00/42199 | 7/2000 | ........... C12N/15/54 |

OTHER PUBLICATIONS

Checa,S. et al., "The 70–kDa heat–shock protein/DnaK chaperone system is required for the productive folding of ribulose–bisphosphate carboxylase subunits in *Escherichia coli*," Eur. J. Biochem, 248, 848–855 (1997).
Soltis, Daniel et al., "The a and B chains of avian retrovirus reverse transcriptase independintly expressed in *Escherichia coli*:Characterization on enzymatic activities," Proc. Natil. Acad. Sci. USA. vol. 85, 3372–3376 (4988).
Kawata, Yasushi et al., "Chaperonin GroE and ADP facilitate the folding of various proteins and protect against heat inactivation," FEBS Letters 345 (1994) 229–232.
Lee, Stephen C. et al., "Effect of Overproduction of Heat Shock Chaperones GroESL and DnaK on Human Procollagenase Production in *Escherichia coli*." The Journal of Biological Chemistry, vol. 267, No. 5, Issue of Feb. 15, pp. 2849–2852, 1992.

Steiger et al., "The production of slouble recombinant proteins in *E. coli* assisted by molecular chaperones," Immunology Methods Manual, Oct. 1996, pp. 40–44.
Wende, Wolfgang, et al., "The Production and Characterization of Artificial Heterodimers of the Restriction Endonuclease EcoRV." Biol. Chem. vol. 377, Oct. 1996, 1 pp. 625–632.
Aiyar, Ashok, et al., "Interaction between Retroviral U5 RNA and the TuC Loop of the tRNA trp Primer is Required for Efficient Inititation of Reverse Transcription", Journal of Virology, Apr. 1992, p. 2464–2472, vol. 66, No. 4.
Baltimore, David, et al., "Viral RNA–Dependent DNA Polymerase" Nature vol. 226, Jun. 27, 1970 (pp. 1209–1211).
Baluda Marcel A., et al., "Anatomy of an Integrated Avian Myeloblastosis Provirus: Structure and Function", Invited Review, Correspondence: E. Premkumar Reddy, Received Jul. 26, 1994; accepted in CRC form Jul. 28, 1994, (14pgs).
Brinkmann, Ulrich, et al., "High–Level Expression of Recombinant Genes in *Escherichia Coli* is Dependent on the Availability of the dnaY Gene Product", Gene, 85 (1989) 109–114, Elsevier, GENE 03325.
Bujard, Hermann, et al., "A T5 Promoter–Based Transcription–Translation System for the Analysis of Proteins in Vitro and in Vivo", Methods in Enzymology, vol. 155, (pp. 416–433).
Bukau, Bernd, et al., "The Hsp70 and Hsp60 Chaperone Machines", Cell., vol. 92, 351–366, Feb. 6, 1998.
Deuerling, Elke et al., "Trigger Factor and DnaK Cooperate in Folding of Newly Synthesized Proteins", Nature, vol. 400, Aug. 12, 1999, (pp. 693–696).
Diamant, Sophia, et al., "Temperature–Controlled Activity of DnaK–DnaJ–GrpE Chaperones: Protein–Folding Arrest and Recovery During and After Heat Shock Depends on the Substrate Protein and the GrpE Concentration", Biochemistry 1998, 37, pp. 9688–9694.
Garcia, George M., et al., "The *E. Coli* dnaY Gene Encodes an Arginine Transfer RNA", Cell, vol. 45, 453–459, May 9, 1986.
Golomb, Miriam, et al., "Endonuclease Activity of Purified RNA–Directed DNA Polymerase from Avian Myeloblastosis Virus", The Journal of Biological Chemistry, vol. 254, No. 5, Issue of Mar. 10, pp. 1606–1613, 1979.
Goloubinoff, Pierre, et al., "Sequential Mechanism of Solubilization and Refolding of Stable Protein Aggregates by a Bichaperone Network" 13732–13737, PNAS, Nov. 23, 1999, vol. 96, No. 24.
Grice, Stuart F.J. Le, et al., "Human Immunodeficiency Virus Reverse Transcriptase", HIV Reverse Transcriptase, (15pgs), (no date).

(Continued)

*Primary Examiner*—Charles L. Patterson, Jr.
(74) *Attorney, Agent, or Firm*—Marilyn Amick; Roche Diagnostics Operations, Inc.

(57) ABSTRACT

The heterologous expression of the reverse transcriptase from the Avian Myeloblastosis Virus (AMV-RT) in prokaryotic cells and in particular *Escherichia coli* (*E. coli*) is described in the present invention. The invention also includes certain measures to simplify the purification of the heterodimeric AMV-RT.

10 Claims, 3 Drawing Sheets

OTHER PUBLICATIONS

Hanahan, Douglas, et al., "Studies on Transformation of *Escherichia Coli* with Plasmids", J. Mol. Biol. (1983) 166, pp. 557–580.

Hartl, F. Ulrich, et al., "Molecular Chaperones in Cellular Protein Folding", Nature, vol. 381, Jun. 13, 1996, pp. 571–580.

Kedzierska, S., "The Role of DnaK/DnaJ and GroEL/GroES Systems in the Removal of Endogenous Proteins Aggregated by Heat–Shock from *Escherichia Coli* Cells", FEBS Letters 446(1999) 331–337.

Kopetzki, Erhard, et al., "Control of Formation of Active Soluble or Inactive Insoluble Bakers' Yeast x–glucosidase PI in *Escherichia Coli* Induction and Growth Conditions", Mol. Gen. Genet (1989) 216:149 155.

Laemmli, U.K., "Cleavage of Structural Proteins During the Assembly of the Head of Bacteriophage T4", Nature vol. 227, Aug. 15, 1970, pp. 680–685.

Leis, Jonathan, et al., "Regulation of Initiation of Reverse Transcription of Retroviruses", Reverse Transcriptase, Department of Biochemistry, Case Western Reserve University School of Medicine, Cleveland, Ohio 44106, pp. 33–47, (1993).

Mogk, Axel, et al., "Identification of Thermolabile *Escherichia Coli* Proteins: Prevention and Reversion of Aggregation by DnaK and ClpB", The EMBO Journal vol. 18, No. 24, pp. 6934–6949, 1999.

Muller, Barbara, et al., "Co–Expression of the Subunits of the Heterodimer of HIV–1 Reverse Transcriptase in *Escherichia Coli*", The Journal of Biological Chemistry, vol. 264, No. 24, Issue of Aug. 25, pp. 13975–13978, 1989.

Pierpaoli, Ezra, et al., "Control of the DnaK Chaperone Cycle by Substoichimetric Concentrations of the Co–Chaperones DnaJ and GrpE" J. Biol Chem vol. 273, No. 12, Issue of Mar. 20, pp. 6643–6649, 1998.

Prasad, Vinayaka R., et al., "Genetic Analysis of Retroviral Reverse Transcriptase Structure and Function", Reverse Transcriptase, Copyright 1993 Cold Spring Harbor Laboratory Press, Department of Microbiology and Immunology, pp. 135–163.

Ricchetti, Miria, et al., "*E. Coli* DNA Polymerase I as a Reverse Transcriptase", The EMBO Journal, vol. 12, No. 2, pp. 387–396, 1993.

Temin, Howard M., "RNA–Dependent DNA Polymerase in Virions of Rous Sarcoma Virus", Nature vol. 226, Jun. 27, 1970, pp. 1211–1213.

Weiss, Robin, et al., "RNA Tumor Viruses", Molecular Bilogy of Tumor Viruses Second Edition, Cold Spring Harbor Laboratory 1984, 24 pgs , pp. 378–423.

Zolkiewski, Michal, et al., "ClpB Cooperates with DnaK, DnaJ, and GrpE in Suppressing Protein Aggregation", A Novel Multi–Chaperone System from *Escherichia Coli*, The Journal of Biological Chemistry, vol. 274, No. 40, Issue of Oct. 1, pp. 28083–28086, 1999.

Fayet, Olivier, et al., "Suppression of the *Escherichia Coli* dnA46 Mutation by Amplification of the groES and grEL Genes", Mol. Gen. Genet (1986) 202: 435–445.

METHOD FOR PRODUCING AN ACTIVE HETERODIMERIC AMV-RT IN PROKARYOTIC CELLS

The invention concerns a method for producing a recombinant active heterodimeric AMV-RT by expressing one or several DNA sequences coding for the α- and/or β-subunit(s) of the AMV-RT in prokaryotic cells under certain growth and induction conditions.

The discovery of the reverse transcriptases in the seventies disproved the "central dogma" of molecular biology on the information transfer from DNA via RNA to protein as a unidirectional process (Termin H. and Mizutani S., 1970 Nature 226:1211–1213; Baltimore D., 1970, Nature 226:1209–1211). The enzymatic characterization of these RNA-dependent DNA polymerases is the basis for current understanding on the amplification cycle of RNA viruses and thus also on the development and spread of diseases that are caused by this type of virus (cancer, AIDS etc.).

However, reverse transcriptases are also a tool for molecular biologists for the synthesis, amplification and cloning of cDNAs (RT-PCR). This technology allows a simplified and accelerated examination of gene expression in eukaryotic cells. After isolating the total mRNA from cell extracts or tissues, the mRNA is translated back into cDNA by the reverse transcriptase and amplified by the subsequent PCR step to enable cloning and characterization. consequently it is not necessary to, on the one hand, elucidate the intron and exon structures of the genes but, on the other hand, it is also possible to examine gene expression in the cell during various life cycles or during the development of diseases (such as cancer).

Reverse transcriptases (RT) from three different retroviruses have hitherto been closely examined: The RT from Moloney Murine Leukemia Virus (M-MLV). This enzyme consists of a single subunit with a molecular weight of 78 kDa (Prasad V. R., 1993 reviewed in *Reverse Transcriptase*, Cold Spring Harbor, N.Y.: Cold Spring Harbor Laboratory Press, 135). In addition an RT from Human Immunodeficiency Virus (HIV) is known. This RT is a heterodimer that is composed of two subunits p66 and p51, the p51 subunit being formed by proteolytic cleavage of p66 (Le Grice S. F. J., 1993 reviewed in *Reverse Transcriptase*, Cold Spring Harbor, N.Y.: Cold Spring Harbor Laboratory Press, 163). In addition RTs are known from Avian Sarcoma-Leukosis Virus (ASLV). The RT obtainable from Avian Myeloblastosis Virus (AMV) also belongs to the ASLV family. This RT is also a heterodimer that is composed of an α-chain with a molecular weight of ca. 63 kDa and a β-chain with a molecular weight of ca. 95 kDa. In this case the α-chain is also formed by proteolytic processing of the β-chain (Golomb M. and Grandgenett D., 1979, *J. Biol. Chem.* 254: 1606–1613; Weiss R. et al., eds. 1984, *Molecular Biology of tumor viruses*, 2$^{nd}$ edition: RNA tumor viruses 1/text. Cold Spring Harbor Laboratory, Cold Spring Harbor, N.Y.).

Whereas the M-MLV-RT is expressed in *E. coli* as a monomer and the HIV-RT as a heterodimer, it has so far not been possible to express the AMV-RT as an active or soluble heterodimer in *E. coli* or other prokaryotes to a satisfactory degree. Although according to WO 00/42199 certain RT variants are expressed in *E. coli* or preferably in eukaryotic insect cells, the desired RT that is obtained in this process mainly consists (ca. 90%) of an insoluble component.

In addition it is difficult to measure a recombinant AMV-RT in crude cell extracts of *E. coli* since, on the one hand, RNA templates are degraded by intrinsic *E. coli* RNases and, on the other hand, *E. coli* strains have a DNA polymerase which also has an RT activity in addition to the DNA polymerase activity (Ricchetti, M. and Huc, H., 1993, *EMBO J.* 12 (2), 387–396). Hence this intrinsic *E. coli* RT activity considerably interferes with the determination of the activity of the recombinant AMV-RT in crude *E. coli* extracts and in fractions from the purification.

Hence the object of the present invention is to provide a recombinant active heterodimeric AMV-RT in adequate amounts.

The object is achieved by a method for producing an active heterodimeric AMV-RT in prokaryotic host cells wherein one or several DNA sequence(s) which code for the α and β subunit or chain of the AMV-RT, are cloned into expression plasmids, the expression plasmids are transformed in prokaryotic cells, the expression of the heterodimeric AMV-RT is induced and the recombinant heterodimeric AMV-RT is purified i.e. isolated from the cells. Suitable genes and DNA sequences are, among others, those which only code for one of the AMV-RT subunits. A portion or the expression product can subsequently be converted by certain measures, such as proteolytic cleavage of the β-chain, into the other subunit. The sequences SEQ ID NO:4 and SEQ ID NO:5 have proven to be particularly suitable for the method according to the invention which generates an active heterodimeric AMV-RT composed of the subunits SEQ ID NO:6 and SEQ ID NO:7.

The structural genes and DNA sequences coding for the subunits of the AMV-RT can either be cloned on different, separate expression plasmids or on one expression plasmid, optionally in the presence of so-called helper plasmids, and expressed in a suitable host cell. Suitable expression plasmids are for example pDS, pKK177-3 or pKKT5. The plasmid pKKT5 in which the respective structural genes are inserted under the control of the T5 promoter is preferred according to the invention. Other potential promoters, which are preferably IPTG-inducible promoters, are for example the lac, lac UV5 or tac promoter. Alternative helper plasmids such as the plasmid pUBS520 and suitable selection markers such as ampicillin or kanamycin are in principle known to a person skilled in the art.

The expression plasmids and optionally other helper plasmids are transformed into a suitable prokaryotic host cell. According to the invention it is preferable to use an *E. coli* strain such as *E. coli* K12 C600, DH5α, LE392, JM83, JM105, NM522, M15, RR1 Δ15, UT5600, TG1, A1200 or the strains *E. coli* B, BL21, HB101. The *E. coli* strain LE392 is particularly preferred according to the invention.

The expression of the heterodimeric AMV-RT can be induced by various measures. In particular certain growth and induction conditions have positive effects on the expression of active AMV-RT. A growth temperature in the range of 10° to 25° C. combined with a low inducer concentration has proven to be advantageous according to the invention. A growth temperature of about 15° C. and an inducer concentration between 0.1 and 0.5 mM, preferably of about 0.15 mM, have proven to be particularly suitable. IPTG (isopropyl-β-D-thiogalactopyranoside) or lactose are preferably used according to the invention as the inducer.

Furthermore it turned out that the soluble expression of AMV-RT in prokaryotic cells can be increased by the co-expression of helper genes. Potential helper genes are in particular the trpT gene which codes for the tryptophan tNRA. In addition chaperone genes are suitable for soluble expression such as the genes coding for GroEL and GroES, GrpE, ClpB, Dnak and DnaJ. The genes for one or several chaperones are then preferably located on a helper plasmid with an inducible promoter; the genes which code for the chaperones GroEL and GroES are under the control of a constitutive promoter on the expression plasmid on which the structural genes for the α and/or β chain are also located. However, it is particularly preferred according to the invention when the genes coding for GroEL and GroES are cloned on the expression plasmid which carries the genes for the α-and β-chain and the genes coding for Dnak, DnaJ, GrpE and ClpB are cloned on a helper plasmid.

In addition to methods that are generally known to a person skilled in the art, it is especially advantageous to use affinity chromatography materials such as metal ion chelating materials or cation exchangers to purify and isolate the recombinant heterodimeric AMV-RT from the cell extract. It is particularly advantageous for the purification of the AMV-RT for the expression products, i.e. the α- as well as the β-chain to be fused with peptide sequences that are able to reversibly bind to particular column materials such as cation exchangers, metal ion chelating materials such as nickel, copper or zinc nitriloacetic acid (NTA) resins. Peptide sequences that are suitable according to the invention can have from two to about 100 amino acids or amino acid derivatives. Peptide sequences which are composed of two to ten amino acids, e.g. arginine residues or histidine residues, have proven to be particularly suitable for the invention. In addition it has also proven to be particularly advantageous to use such peptide sequences comprising eight arginine or six histidine residues. In addition commercially available peptide sequences such as Strep-tag® (IBA GmbH, Göttingen/Germany) or GST-tag (Pharmacia, Uppsala/Sweden) are also suitable for the method according to the invention.

Figure 1:
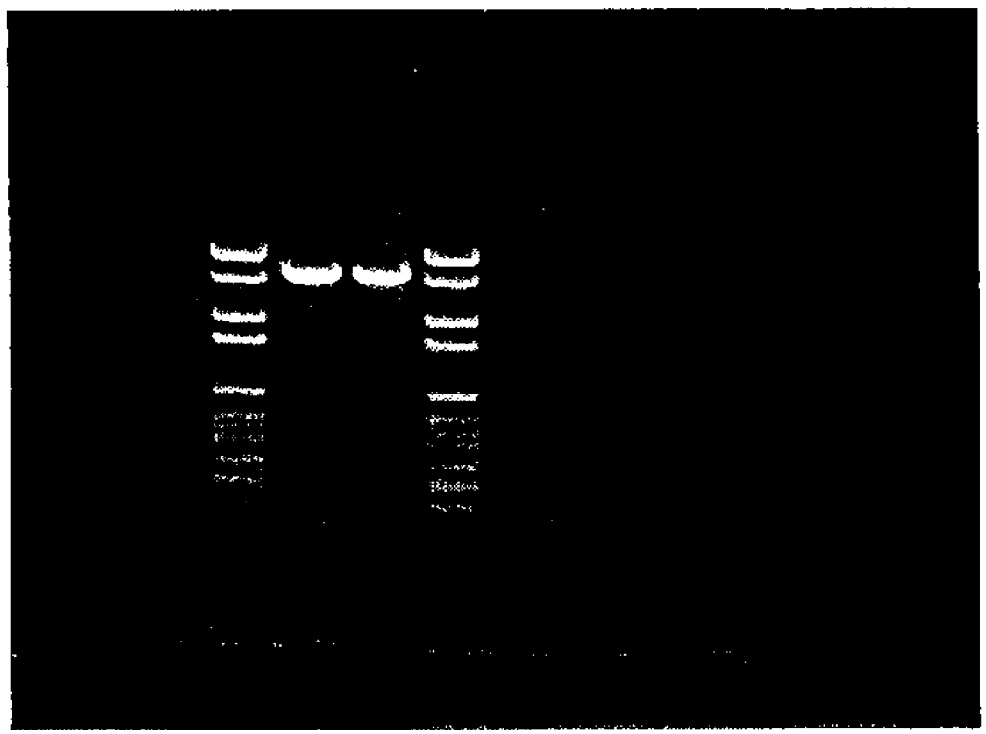
FIG. 1 shows the amplification product of the RT-PCR having a size of 1.8 kb, which was obtained using native purified AMV-RT (lane 2) and AMV-RT that was obtained by recombinant means (lane 3). Lanes 1 and 4 show a DNA molecular weight marker VI (cat. No. 1062590, Roche Molecular Biochemicals).

The invention is further elucidated by the following examples:

1. EXAMPLE

Isolation of Genes Which Code for the α- chain and β-chain

The data bank sequence (MEDLINE ID 94366722, Baluda et al., 1994) was used to design oligonucleotide primers for the isolation of the β-chain (see SEQ ID NO:1 and 2). A EcoRI restriction endonuclease cleavage site was incorporated at the 5' end and a PstI restriction cleavage site was incorporated at the 3' end for the subsequent cloning into vectors. In addition a further 3' primer was designed (see SEQ ID NO:3) which enables the isolation of the α-chain. Both chains were fished by means of PCR from a virus lysate (ATCC VR-265) by means of RT-PCR as well as from an E. coli clone (ATCC 31990) which carries the β-chain on a plasmid. The PCR mixtures were applied to a 1% agarose gel, the PCR fragments of ca. 1715 bp for the α-chain and ca. 2570 bp for the β-chain were isolated from the agarose gel (QIAEX II, Gel Extraction Kit, Qiagen/Germany), cleaved with the restriction endonucleases mentioned above and cloned into a vector fragment of pUC19 that had also been linearized with EcoRI and PstI and isolated. For this 1 µl (20 ng) vector fragment and 3 µl (100 ng) PCR fragment, 1 µl 10×ligase buffer (Maniatis et al., 1989 Molecular Cloning: A Laboratory Manual, second Edition, Cold Spring Harbor Laboratory Press NY (USA.), vol. 27), 1 µl T4 DNA ligase, 4 µl sterile $H_2O_{bidistilled}$ were pipetted, carefully mixed and incubated overnight at 16° C. The cloned genes were subsequently examined by means of restriction analysis and sequencing. The sequences are shown in SEQ ID NO:4 (α-chain) and SEQ ID NO: 5 (β-chain).

Comparison with the data bank sequence (MEDLINE ID 94366722, Baluda, M. A., and Reddy, E. P., 1994, Oncogene 9:2761–2774) yielded a homology of 98.8% at the DNA level for the α-chain as well as for the β-chain. When the resulting amino acid sequences are compared, it becomes apparent that most substitutions at the DNA level are so-called silent mutations i.e. do not lead to amino acid substitutions. Only three base substitutions also resulted in amino acid substitutions but they are found reproducibly in each isolated PCR product. These are the substitutions Arg273Met, Arg304Gln and Asp495Glu. The amino acid sequences of both chains are shown in SEQ ID NO:6 (α-chain) and SEQ ID NO:7 (β-chain).

2. EXAMPLE

Expression of the α-chain and β-chain Without Fused Peptide Sequences (tags)

2.1. Construction of the Expression Plasmids pAMV-α and pAMV-β

In order to express the AMV-RT, the genes for both chains were cloned separately into expression vectors in such a manner that the structural genes were each inserted in the correct orientation under the control of the T5 promoter. For this the respective structural gene for the α-chain and the β-chain were cut out of the plasmid pUC19 by EcoRI and PstI, the restriction mixtures were separated by agarose gel electrophoresis and the 1715 bp fragment of the α-chain and the 2570 bp fragment of the β-chain were isolated from the agarose gel. The expression plasmid pKKT5, which is formed from pKK177-3 (Kopetzki et al., 1989, Mol. Gen. Genet. 216: 149–155) by replacing the tac promoter with the T5 promoter from pDS (Bujard et al., 1987, Methods Enzymol. 155: 416–433), was used for the expression. The EcoRI restriction endonuclease cleavage site in the sequence of the T5 promoter was removed by two point mutations. The resulting expression plasmid was cut with EcoRI and PstI for the insertion of the genes for the AMV-RT, the restriction mixture was separated by agarose gel electrophoresis and the resulting vector fragment of ca. 2500 bp was isolated from the agarose gel. The vector fragment obtained in this manner was separately ligated as described above with the genes for the α-chain and the β-chain described in example 1. The correct insertion of the genes was checked by restriction control and sequencing. The resulting plasmid pAMV-α and pAMV-β was firstly separately cotransformed with the helper plasmid pUBS520 for expression control in various *E. coli* strains. It is conceivable in this case that the α-chain and the β-chain could be separately expressed in order to obtain αα- and ββ-homodimers. The helper plasmid pUBS520 (Brinkmann et al., 1989, Gene 85: 109–114) carries inter alia the lacI$^q$ gene which codes for the lac repressor and the dnaY gene which codes for the rare tRNA$^{Arg}$ in *E. coli* which recognizes the codons AGA and AGG (Garcia et al., 1986, Cell 45: 453–459). The kanamycin resistance gene from the transposon TN903 was used as a selection marker.

2.2 Separate Transformation of the Expression Plasmids pAMV-α and pAMV-β in *E. coli*

Competent cells of various *E. coli* strains were prepared according to the method of Hanahan (*J. Mol. Biol.* 1983, vol. 166, 557). 200 µl of *E. coli* LE392 cells prepared in this manner were admixed with 20 ng isolated expression plasmid pAMV-α DNA or pAMV-β DNA and 40 ng helper plasmid DNA. After 30 min incubation on ice a heat shock (90 sec. at 42° C.) was carried out. Subsequently the cells were transferred to 1 ml LB medium and incubated for 1 hour at 37° C. in LB medium for the phenotypic expression. Aliquots of this transformation mixture were plated out on LB plates containing ampicillin and kanamycin as selection markers and incubated for 15 hours at 37° C.

2.3 Expression of the Gene for the α-chain in *E. coli*

In order to express the gene which codes for the α-chain of the AMV-RT, plasmid-containing clones were inoculated in 3 ml LB$_{ampkan}$ medium and incubated at 30° C. in a shaker. At an optical density of 0.5 (measured at 550 nm, OD$_{550}$) the cells were induced with 0.5 mM IPTG and incubated for 4 h at 30° C. in a shaker. Subsequently the optical density of the individual expression clones was determined, an aliquot which corresponded to an OD$_{550}$ of 5.0/ml was removed and the cells were centrifuged (10 min, 6000 rpm, 4° C.). The cell pellet was resuspended in 400 µl TE buffer (50 mM TRIS/50 mM EDTA, pH 8.0), the cells were disrupted by ultrasound and the soluble protein fraction was separated from the insoluble protein fraction by centrifugation (10 min, 14000 rpm, 4° C.). Application buffer containing SDS and β-mercaptoethanol was added to all fractions and the proteins were denatured by boiling (5 min 100° C.). Afterwards 10 µl of each was analysed by means of an analytical SDS gel (10%) (Laemmli U. K., 1970, *Nature* 227: 555–557).

Analysis of the SDS gel shows a clear overexpression of the α-chain. A strongly overexpressed additional band is seen at ca. 63 kDa which is not observed with the non-induced control clones or the induced control clones which do not contain plasmid. A small portion of the overexpressed α-chain appears in the soluble protein fraction whereas the major amount is formed as an insoluble expressed protein.

2.4 Expression of the Gene of the β-chain in *E. coli*

In order to express the gene which codes for the β-chain of the AMV-RT, 3 ml LB$_{ampkan}$ medium was inoculated with plasmid-containing clones and incubated at 30° C. in a shaker. At an OD$_{550\ nm}$ of 0.5 the cells were induced with 0.5 mM IPTG and incubated for 4 h at 30° C. in a shaker. Subsequently the optical density of the individual expression clones was determined, an aliquot which corresponded to an OD$_{550}$ of 5.0/ml was removed and the cells were centrifuged (10 min, 6000 rpm, 4° C.). The cell pellet was resuspended in 400 µl TE buffer (50 mM TRIS/50 mM EDTA, pH 8.0), the cells were disrupted by ultrasound and the soluble protein fraction was separated from the insoluble protein fraction by centrifugation (10 min, 14000 rpm, 4° C.). Application buffer containing SDS and β-mercaptoethanol was added to all fractions and the proteins were denatured by boiling (5 min 100° C.). Afterwards 10 µl of each was analysed by means of an analytical SDS gel (8%) (Laemmli U. K., 1970, *Nature* 227: 555–557).

Analysis of the SDS gel shows a clear overexpression of the β-chain. A strongly overexpressed additional band is seen at ca. 95 kDa which is not observed with the non-induced control clones or the induced control clones which do not contain plasmid. The majority of the overexpressed β-chain appears in the insoluble protein fraction, however, a slight overexpression is also seen in the soluble protein fraction.

2.5 Expression of Both Chains on Separate Plasmids in a Cell

In order to express both chains in one cell, the lacI$^q$ expression cassette and the dnaY expression cassette must firstly be recloned from the helper plasmid pUBS520 onto the expression plasmids. The lacI$^q$ expression cassette was cloned onto pAMV-α and the dnaY expression cassette was cloned onto the expression plasmid pAMV-β. In order to ensure a stable multiplication of the expression plasmids, the ampicillin resistance gene from pAMV-α was replaced by the kanamycin resistance gene from pUBS520. The resulting expression plasmids pAMV-α$_{lacIq}$ and pAMV-β$_{dnaY}$ were subsequently cotransformed in various *E. coli* expression strains.

In order to express the genes which code for the α-chain and the β-chain of the AMV-RT, 3 ml LB$_{ampkan}$ medium was inoculated with plasmid-containing clones and incubated at 30° C. in a shaker. At an OD$_{550\ nm}$ of 0.5 the cells were induced with 0.5 mM IPTG and incubated for 4 h at 30° C. in a shaker. Subsequently the optical density of the individual expression clones was determined, an aliquot which corresponded to an OD$_{550\ nm}$ of 5.0/ml was removed and the cells were centrifuged (10 min, 6000 rpm, 4° C.). The cell pellet was resuspended in 400 µl TE buffer (50 mM TRIS/50 mM EDTA, pH 8.0), the cells were disrupted by ultrasound and the soluble protein fraction was separated from the insoluble protein fraction by centrifugation (10 min, 14000 rpm, 4° C.). Application buffer containing SDS and β-mercaptoethanol was added to all fractions and the proteins were denatured by boiling (5 min 100° C.). Afterwards 10 µl of each was analysed by means of an analytical SDS gel (8%) (Laemmli U. K., 1970, *Nature* 227: 555–557).

Analysis of the SDS gel surprisingly shows a clear overexpression of the α- and β-chain. Strongly overexpressed additional bands are seen at ca. 63 kDa and ca. 95 kDa which are not observed with the non-induced control clones or the induced control clones which do not contain plasmid. The distribution of the bands in the soluble and insoluble fraction is like that of the experiments in which both chains were expressed separately. The expression output of both chains is overall somewhat less than for separate expression.

3. EXAMPLE

Expression of the α-chain and β-chain with Fused Tags to Simplify the Purification 3.1 Production of Various Fusion Proteins In order to efficiently purify the recombinant AMV-RT heterodimers, suitable peptide sequences, so-called tags were fused to the 5' end of both chains. Tags enable affinity chromatographies to be carried out. A series of two affinity chromatographies which are each specific for one of the two tags additionally allows the isolation of pure heterodimers (Wende W. et al., 1996, *Biol. Chem.* 377, 625–632). Appropriate primer designs were used to attach eight arginine residues to the α-chain and six histidine residues to the β-chain by means of PCR reactions. The sequences of the sense primers are shown in SEQ ID NO:8 (5' primer for the α-chain) and SEQ ID NO:9 (5' primer for the β-chain). The oligonucleotides of SEQ ID NO:2 (β-chain) and SEQ ID NO:3 (α-chain) which had already been used for gene isolation were used as antisense primers.

The PCR mixtures were applied to a 1% agarose gel, the PCR fragments of 1739 bp for the α-chain and 2597 bp for the β-chain were isolated from the agarose gel (QIAEX II, Gel Extraction Kit, Qiagen, Germany), cleaved with the restriction endonucleases EcoRI and PstI and cloned into a vector fragment of the preferred expression plasmid that had also been linearized with EcoRI and PstI and isolated. For this 1 μl (20 ng) vector fragment and 3 μl (100 ng) PCR fragment, 1 μl 10×ligase buffer (Maniatis et al., 1989 Molecular Cloning: A Laboratory Manual, second Edition, Cold Spring Harbor Laboratory Press NY (USA), vol. 27), 1 μl T4 DNA ligase, 4 μl sterile $H_2O_{bidistilled}$ were pipetted, carefully mixed and incubated overnight at 16° C. The cloned genes were subsequently examined by means of restriction analysis and sequencing. The resulting Expression Plasmids were named pAMV-$\alpha_{lacIq-Arg}$ and pAMV-$\beta_{dnaY-His}$.

3.2 Transformation of the expression plasmids pAMV-$\alpha_{lacIq-Arg}$ and pAMV-$\beta_{dnaY-His}$ in Various *E. coli* Expression Strains Competent cells of various *E. coil* strains were prepared according to the method of Hanahan (*J. Mol. Biol.* 1983, vol. 166 pp. 557) (see example 2.2).

3.3 Expression of Both Chains with Fused Tags on Separate Plasmids in a Cell

In order to express both chains with tags in a cell, various *E. coli* expression strains were cotransformed with the expression plasmids pAMV-$\alpha_{lacIq-Arg}$ and pAMV-$\beta_{dnaY-His}$.

In order to express the genes which code for the α-chain with an Arg-tag and the β-chain with an His-tag of the AMV-RT, 3 ml $LB_{ampkan}$ medium was inoculated with plasmid-containing clones and incubated at 30° C. in a shaker. At an $OD_{550}$ of 0.5 the cells were induced with 0.5 mM IPTG and incubated for 4 h at 30° C. in a shaker. Subsequently the optical density of the individual expression clones was determined, an aliquot which corresponded to an $OD_{550}$ of 5/ml was removed and the cells were centrifuged (10 min, 6000 rpm, 4° C.). The cell pellet was resuspended in 400 μl TE buffer (50 mM TRIS/50 mM EDTA, pH 8.0), the cells were disrupted by ultrasound and the soluble protein fraction was separated from the insoluble protein fraction by centrifugation (10 min, 14000 rpm, 4° C.). Application buffer containing SDS and β-mercaptoethanol was added to all fractions and the proteins were denatured by boiling (5 min 100° C.). Afterwards 10 μl of each was analysed by means of an 8% analytical SDS gel (Laemmli U. K., 1970, *Nature* 227: 555–557).

Analysis of the SDS gel surprisingly shows a clear overexpression of the α- and β-chain. Strongly overexpressed additional bands are seen at ca. 63 kDa and ca. 95 kDa which are not observed with the non-induced control clones or the induced control clones which do not contain plasmid. The distribution of the bands in the soluble and insoluble fraction is like that of the experiments in which both chains were expressed separately without tags in one cell.

3.4 Expression of Both Chains with Fused Tags on a Plasmid

If the genes for the α- and β-chain of the AMV-RT are distributed on two plasmids, differences in the stability of these plasmids could lead to the production of different amounts of the respective chains and thus to a lower yield of αβ-chain heterodimer. Hence with the exception of the gene for β lactamase, the entire genetic information of the two plasmids pAMV-$\alpha_{lacIq-Arg}$ and pAMV-$\beta_{dnaY-His}$ was combined on a single plasmid pAMV-αβ-1. This plasmid was constructed by inserting the SspI-AflIII fragment of pAMV-$\beta_{dnaY-His}$ containing the sequence for the T5 promoter, the gene coding for the β-chain with an N-terminal His tag, the sequence for the rrnB terminator and the dnaY gene, into the SalI cleavage site of pAMV-$\alpha_{lacIq-Arg}$ which contains the sequence for the T5 promoter, the gene coding for the α-chain with an N-terminal Arg-tag, the sequence for the rrnB terminator, the kanamycin resistance gene and the lacI$^q$ gene. For this purpose 1 μg each of the expression plasmids pAMV-$\alpha_{lacIq-Arg}$ and pAMV-$\beta_{dnaY-His}$ were cleaved with the restriction endonucleases described above according to the manufacturer's instructions, the restriction mixtures were separated in a 1% agarose gel and the 4124 bp SspI-AflIII fragment of pAMV-$\beta_{dnaY-His}$ and the 6024 bp fragment of pAMV-$\alpha_{lacIq-Arg}$ were isolated from the agarose gel (QIAEX II, Gel Extraction Kit, Qiagen/Germany). The non-compatible ends were prepared with Klenow polymerase (Roche Diagnostics GmbH) according to the manufacturer's instructions and the two fragments were ligated together as described above. The resulting new expression plasmid pAMVαβ-1 was examined by means of restriction analysis.

The correct expression plasmid according to restriction analysis was transformed in the *E. coli* K-12 strain LE392 as described above and subjected to an expression control. The protein content of the cells after 4 hours growth under induced conditions was subsequently examined by means of SDS-PAGE. According to SDS-PAGE analysis the level of the expression output and the relative proportion of soluble and insoluble fractions are comparable to the expression of the genes for the α- and β-chain on separate plasmids, but the amount of expressed α- and β-chain appears to be more homogeneous.

Furthermore the Arg-tag of the α-chain was replaced by a His-tag like that of the β-chain for the purification procedure. For this purpose an intermediate construct pAMV-$\alpha_{lacIq-His}$ was prepared in which the EcoRI-NheI fragment from pAMV-$\alpha_{lacIq-Arg}$ was replaced by the EcoRI-NheI fragment from pAMV-$\beta_{dnaY-His}$. Subsequently, like the construction of pAMVαβ-1, the entire genetic information of the two plasmids pAMV-$\alpha_{lacIq-His}$ and pAMV-$\beta_{dnaY-His}$ with the exception of the gene for β lactamase was combined on a single plasmid pAMVαβ-2. The new expression vector was named pAMVαβ-2. Cells were transformed as described above with pAMVαβ-2and subjected to an expression control under standard conditions. The expression output was not increased under these conditions.

4. EXAMPLE

Expression Optimization 4.1 Increase of the Expression of Active AMV-RT by Changing the Expression Conditions Particular growth and induction conditions have positive effects on the expression of active AMV-RT. Afterwards the growth temperature was lowered from 30° C. to 15° C. during the induction phase, the IPTG concentration was reduced from 0.5 mM to 0.15 mM to induce expression and the induction time was increased from 4 h to 26 h. The protein content of the cells after the induction phase was examined as described above by SDS polyacrylamide gel electrophoresis.

Afterwards the total expression yield of α- and β-chain was, as expected, substantially reduced in the SDS-PAGE analysis, but the content of soluble expressed α- and β-chain was considerably increased in comparison to the expression experiments under standard growth and induction conditions. This increase in the expression of active AMV-RT was also confirmed in the subsequent purification and activity determination.

4.2 Increasing the Expression of Active AMV-RT by Coexpression of Helper Genes 4.2.1. Coexpression of the Gene for the Tryptophan-tRNA (tRNA$^{trp}$)

One property of the AMV-RT is to use an endogenous cell tRNA for tryptophan (tRNA$^{trp}$) as a primer for the polymerase reaction after infection of a eukaryotic host cell (Leis et al., 1993, in: Reverse Transcriptase, Cold Spring Harbor Monograph Series, eds.: Skala, A. M. and Goff, S. P., Cold Spring Harbor, N.Y. (USA), 33–48). However, whether the endogenous E. coli tRNA$^{trp}$ can be used by the AMV-RT as a primer has not been proven. In E. coli the tRNA$^{trp}$ is only coded by a single gene trpT, the expression of which is adapted to the normal requirements of the cell. In order to exclude a potential deficiency of tRNA$^{trp}$ in the cell, the trpT gene according to SEQ ID NO:10 was isolated by means of PCR from E. coli LE392 (the primers used for this are shown in SEQ ID NO:11 and 12), recleaved with PstI for insertion into pAMV-α$_{lacIq-His}$ and ligated into the vector fragment of pAMV-α$_{lacIq-His}$ that was also linearized with PstI as described above. Clones which have integrated the trpT gene at the PstI restriction endonuclease cleavage site were checked by means of restriction analysis and sequencing. In this intermediate construct pAMV-α$_{lacIq-His-trpT}$ the gene for the α-chain and the gene for the E. coli tRNA$^{trp}$ form one transcription unit, the expression of which is regulated by the IPTG-inducible T5 promoter. Subsequently, similarly to the construction of pAMVαβ-1 or pAMVαβ-2, the entire genetic information of the two plasmids pAMV-α$_{lacIq-His-trpT}$ and pAMV-β$_{dnaY-His}$ with the exception of the gene for β-lactamase was combined on a single plasmid pAMVαβ-3. Cells were transformed as described above with pAMVαβ-3 and subjected to an expression control using the modified expression conditions. Afterwards the yield of active AMV-RT is significantly increased.

4.2.2. Coexpression of Chaperone Genes

In E. coli there are two main chaperone systems comprising the GroESL machinery and a 4 component system consisting of DnaK, DnaJ, GrpE and ClpB (Kedzierska, 1999). Both systems play an important role in the correct folding of newly formed proteins as well as in the renaturing of proteins that have aggregated as a result of stress (Hartl F. U., 1996, Nature 381, 571–580; Bukau H. and Horwich A. L., 1998, Cell 92, 351–366; MogK A. et al., EMBO J. 18, 6934–6949; Zolkiewski M., 1999, J. Biol. Chem. 274, 28083–28086; Goloubinoff P. et al., 1999, Proc. Natl. Acad. Sci. USA 96, 13732–13737).

In a first step the groESL operon from E. coli should be overexpressed in the AMV-RT production strains. For this the EcoRI-HindIII fragment from pOF39 (Fayet O., Louarn J.-M., Georgopoulos C., 1986, Mol. Gen. Genet. vol. 202, pp. 335–345 was integrated in the SspI cleavage site of the plasmid pAMV-β$_{dnaY-His}$. Non-compatible ends were prepared with Klenow polymerase (Roche Diagnostics) according to the manufacturer's instructions before ligation. The sequence of groESL is shown in SEQ ID NO:13. In this new construct pAMV-β$_{dnaY-His-groESL}$, the groESL operon forms an artificial transcription unit containing the 3'-situated gene for β lactamase. The expression is then either under the control of the endogenous bla constitutive promoter that is now on the 5' side of the groESL operon and/or under the control of the σ$^{32}$-dependent promoter of the groESL operon. Subsequently the entire genetic information of the two expression plasmids pAMV-α$_{lacIq-His-trpT}$ and pAMV-β$_{dnaY-His-groESL}$ with the exception of the gene for β-lactamase was again combined as described above on a single plasmid pAMVαβ-4.

Cells were transformed with pAMVαβ-4 as described above and subjected to an expression control under the modified expression conditions. The co-overproduction of GroESL results in an increase of the biomass and of the amount of active AMV-RT. Three to four-fold higher values were obtained compared to the previously best production strains after purification and activity testing.

After the co-overproduction of GroESL in the AMV-RT production strains had proven to be a positive measure, the other main chaperone system of E. coli was additionally co-overproduced in a second step. In addition to the supposed general advantages of this co-overproduction this could compensate for a disadvantage of the GroESL machinery i.e. its exclusion volume of circa 65 kDa (Deuerling E. et al., 1999, Nature 400, 693–696). This should be particularly important for the correct folding of the β-chain of the AMV-RT (93 kDa) provided it cannot be divided into single domains that are formed independently of one another. The genes DnaK, DnaJ and GrpE were combined in an artificial operon corresponding to the physiological combination (Diamant S. and Goloubinoff P., 1998, Biochemistry 37, 9688–9694; Pierpaoli E. V. et al., 1998, J. Biol. Chem. 273, 6643–6649), whereas the gene for ClpB forms its own transcription unit. Both transcription units were placed under the control of IPTG-inducible T5 promoters in order to coordinate the expression with the genes for the subunits of the AMV-RT.

For technical reasons the cloning process required a number of intermediate steps on the path to the final construct pCHAP-5. Thus the pKKT5 derivatives pCHAP-1 and pCHAP-2 were firstly constructed. pCHAP-1 contains the genetic information for the dnaKJ operon from E. coli starting with the start codon for dnaK up to the stop codon for dnaJ; pCHAP-2 carries the artificial transcription unit from the coding regions of the genes for GrpE and ClpB as an insert; the corresponding DNA fragments were amplified by PCR from the genomic DNA of E. coli K12KE392. The sequence of the dnaKJ operon is shown in SEQ ID NO:14, the corresponding primers used to isolate the dnaKJ operon are shown in SEQ ID NO:15 and 16. The sequence of the grpE gene is shown in SEQ ID NO:17, the corresponding primers for the isolation of the grpE gene are shown in SEQ ID NO:18 and 19. The sequence of the clpB gene is shown in SEQ ID NO:20, the corresponding primers for the isolation of the clpB gene are shown in SEQ ID NO:21 and 22. In order to construct pCHAP-1 the PCR fragment containing the dnaKJ operon was recleaved with SmaI and BamHI and, as described above, ligated into a vector fragment of pKKT5 which had also been linearized with SmaI and BamHI. pCHAP-2 was constructed by means of a three-fold ligation with the EcoRI-PstI fragment of the grpE gene, the PstI-HindIII fragment of the clpB-gene and a vector fragment of pKKT5 linearized with EcoRI and HindIII. p-CHAP-3 in which the clpB gene is present alone as a transcription unit, is derived from pCHAP-2 by ligating the PstI-HindIII fragment from pCHAP-2 into the vector fragment of pKKT5 linearized with EcoRI and HindIII as described above. Before the ligation reaction the non-compatible ends of the two fragments were prepared with Klenow polymerase (Roche Diagnostics) according to the manufacturer's instructions. pCHAP-4 is a pCHAP-1 derivative whose insert was extended by the grpE gene from pCHAP-2 and thus the artificial transcription unit comprises the genes for DnaK, DnaJ and GrpE. As a result of the Shine Dalgarno sequence which is suboptimal in this case, the expression of grpE should be reduced compared to pCHAP-2 and thus be better adapted to the expression of dnaKJ (Diamant & Goloubinoff, 1998; Pierpaoli et al., 1998). In order to construct pCHAP-4 the EcoRI-AvaI fragment from pCHAP-2 was inserted into the BamHI cleavage site of pCHAP-1 after the non-compatible ends of the two fragments had been prepared with Klenow polymerase (Roche Diagnostics) according to the manufacturer's instructions. The final construct p-CHAP-5 is a pCHAP-4 derivative which contains the insert of pCHAP-3 as additional genetic information. For this the BspLU11I-NdeI fragment in pCHAP-4 was replaced by the BspLU11I-SspI fragment from pCHAP-3 by restriction and ligation as already described several times. In order to ensure the compatibility of the ends, the overhanging ends generated by NdeI were previously filled in with Klenow polymerase (Roche Diagnostics) according to the manufacturer's instructions.

The effect of combining the expression plasmid pAMVαβ-4 with the various helper plasmids pCHAP-1 to 5 on the overproduction of active AMV-RT was examined. At least under the modified standard expression conditions all helper plasmids considerably increased the previous yields of active AMV-RT and as expected the helper plasmid pCHAP-5 gave the best result. This was confirmed by SDS-PAGE as well as by subsequent purification and activity determination.

5. EXAMPLE

Analytical Methods 5.1. Test for Reverse Transcriptase Activity (Test A)

During the purification, the reverse transcriptase activity in the fractions was detected by means of a non-radioactive test system. The "reverse transcriptase assay non-radioactive" (Roche Molecular Biochemicals, cat. No. 1468120) was used for this. The incubation period was shortened to 30 minutes.

5.2. Test for Reverse Transcriptase Activity (Test B)

The specific reverse transcriptase activity of the pools was determined by a radioactive test system. Reverse transcriptase activity was determined in a test volume of 100 µl (50 mM Tris/HCl, pH 8.3 (37° C.), 40 mM KCl, 6 mM MgCl$_2$, 0.5 mM dTTP, 0.04 OD$_{260}$ nm poly (A)×dT$_{15}$, 0.1 µM [3H]-dTTP). AMV-RT (5 µl) was added in suitable dilutions. After incubating for 10 min at 37° C., the reaction was stopped with 10% TCA solution (500 µl). The radioactively-labelled product that formed was washed on a nitrocellulose filter after precipitation. The incorporation rate of radioactivity was measured in a scintillation counter and the RT activity of the sample was calculated. One enzyme unit was defined as the amount of AMV-RT which incorporated 1.0 nMol TMP into acid insoluble product in 10 min at 37° C.

5.3. Test for DNA Polymerase

The activity of DNA polymerase from E. coli was determined by measuring the nick translation. The DNA polymerase was detected by means of a non-radioactive nick translation test. The nick translation was carried out in a test volume of 50 µl (50 mM Tris/HCl, pH 7.5, 10 mM MgCl$_2$, 0.1 mM DTE, 28.875 µM DIG-dUTP, 1.444 µM bio-16-dUTP, 95.865 µM dTTP, 20 µM dATP, 20 µM dCTP, 20 µM dGTP, 1 µg pBR322, 1 pg DNaseI). After adding the samples (1 µl) the reaction mixture was incubated for 30 min at 37° C. Afterwards the reaction mixture was transferred to streptavidin-coated microtitre plates. Subsequent treatment and evaluation of the test was carried out analogously to the "reverse transcriptase assay, non-radioactive" (Roche Molecular Biochemicals, Cat. No. 1468120).

5.4 Test for Contaminating Activities

The test for the presence of contaminating foreign activities was carried out in a solution composed of 10 mM Tris/HCl, pH 7.5, 10 mM MgCl$_2$, 1 mM DTE.

Suitable samples of the individual enzyme fractions were incubated with the corresponding nucleic acids. So-called nicking activity was detected by incubation with the plasmid pBR322 (1 µg) for 2–16 hours at 37° C. Unspecific nucleases were detected by incubation with lambda-DNA/EcoRI, HindIII (1 µg) for 2–16 hours at 37° C. Unspecific RNases were detected by incubation for 2–4 hours at 37° C. with MSII-RNA (5 µg).

For the test for contamination by exonucleases, the samples were incubated for 4 hours at 37° C. with 4 µg [3H]-labelled DNA and afterwards the released [3H]-labelled nucleotides were determined.

6. EXAMPLES

Purification and Functional Test 6.1. AMV-RT from E. coli LE392 pAMV-α$_{lacIq\text{-}Arg}$/pAMV-β$_{dnaY\text{-}His}$ Construct 6.1.1. Purification E. coli cells which overexpress both chains of the AMV-RT (see above) were used as the starting material to purify the recombinant AMV-RT.

The AMV-RT was purified at 4° C. The purification was carried out by chromatographic methods after cell lysis and separation of the nucleic acids. The purification process yields a recombinant AMV-RT which is free of contaminating enzyme activities and in RT-PCR has the same functionality as an AMV-RT purified from native material.

Buffer
buffer A: 50 mM Tris/HCl, pH 7.9, 0.5 M KCl, 0.02% Triton X-100, 20% glycerol,
buffer B: 20 mM Tris/HCl, pH 7.9, 0.25 M KCl, 0.02% Triton X-100, 10% glycerol,
buffer C: 20 mM Tris/HCl, pH 7.9, 0.25 M KCl, 0.02% Triton X-100, 10% glycerol, 1 M imidazole,
buffer D: 50 mM Tris/HCl, pH 8.2, 0.1 mM EDTA, 1 mM DTT, 0.02% Triton X-100, 10% glycerol,
buffer E: 20 mM potassium phosphate, pH 7.1, 0.1 mM EDTA, 1 mM DTT, 0.02% Triton X-100, 10% glycerol,
storage buffer: 200 mM potassium phosphate, pH 7.2, 2 mM DTT, 0.2% Triton X-100, 50% glycerol.

Cell Lysis 200 ml buffer A was added to ca. 50 g E. coli LE392 cells (pAMV-α$_{lacIq\text{-}Arg}$/pAMV-β$_{dnaY\text{-}His}$) which were thawed and suspended. Two tablets of Complete (Roche Molecular Biochemicals, cat. No. 1697498) were added to the suspension. Subsequently the cells were lysed by means of ultrasound (Branson sonicator) while cooling (temperature: <10° C.). The degree of lysis of the cell suspension that was achieved was typically 40–50%.

Precipitation of Nucleic Acids

Afterwards the nucleic acids were removed by means of polymin precipitation. 5 ml of a 10% polymin P solution was added dropwise. If the precipitation was incomplete, further dropwise addition was carried out. After incubation for 30 min at 4° C., centrifugation was carried out (30 min, 13000 rpm, 4° C.).

Chromatographic Purifications

Affinity chromatography on a Ni-chelate column: The clear centrifugation supernatant was diluted with buffer B (1+1) and absorbed to a nickel-loaded chelating sepharose ff column (2.6 cm×10 cm, Pharmacia) which had been equilibrated with buffer B, it was then washed with ca. 500 ml buffer B, afterwards with 200 ml buffer B+10 mM imidazole and 200 ml buffer B+20 mM imidazole. The enzyme was eluted with a linear gradient of buffer B+20 mM imidazole and buffer C in a total volume of 500 ml. The flow rate was 5 ml per minute, the fraction size was 20 ml per fraction. The enzyme eluted between 50 mM and 200 mM imidazole. The pool of active fractions was dialysed against buffer D.

Chromatography on Heparin-sepharose

The dialysed pool was subsequently absorbed to a heparin-sepharose ff column equilibrated with buffer D (1.6 cm×10 cm, Pharmacia) and washed with ca. 200 ml buffer D, then with ca. 200 ml buffer D+300 mM KCl. The enzyme was eluted with a linear gradient of buffer D+300 mM KCl and buffer D+1 M KCl in a total volume of 200 ml. The flow rate was 2.5 ml per min, the fraction size was 10 ml. The AMV-RT eluted at a KCl concentration of 500 mM to 700 mM.

Chromatography on S-sepharose ff

The RT-active fractions were pooled and dialysed against buffer E. The dialysate was loaded onto a S-sepharose ff column equilibrated with buffer E (1.6 cm×10 cm, Pharmacia). After washing with ca. 200 ml buffer E, the enzyme was eluted with a linear gradient of buffer E and buffer E+1 M KCl in a total volume of 400 ml. The flow rate was 2.5 ml per minute, the fraction size was 10 ml.

Chromatography on Hydroxylapatite

The RT-active fractions were pooled and dialysed against buffer E. The dialysate was loaded onto a HA-ultrogel column equilibrated with buffer E (1.6 cm×10 cm, Biosepra). After washing with ca. 200 ml buffer E, the enzyme was eluted with a linear gradient of buffer E and buffer E+0.5 M potassium phosphate in a total volume of 400 ml. The flow rate was 2.5 ml per minute, the fraction size was 10 ml.

The RT-active fractions were pooled and dialysed against storage buffer. Application buffer containing SDS and β-mercaptoethanol was added to the purified protein and the sample was denatured by boiling (5 min, 100° C.). Subsequently 20 μl aliquots were analysed by an analytical SDS gel (4–20%) (Laemmli U K., 1970, Nature 227: 555–557). The α- and β-subunits of AMV-RT were found in equimolar ratios.

The described method yields a stable AMV-RT with an equimolar distribution of the α- and β-subunits. The enzyme obtained is functional in RT-PCR.

6.1.2. Functional Test in RT-PCR

The recombinant AMV reverse transcriptase that was obtained was examined in a functional test. The functional test consisted of a reverse transcription (RT) coupled with a polymerase chain reaction (PCR). For this 5 units of the recombinant AMV reverse transcriptase was used like the enzyme mixture of the Titan TM One Tube PCR System (cat. No. 1888382, Roche Molecular Biochemicals). A 1.8 kb fragment of the human dystrophin gene was amplified. 10 ng human muscle RNA was used as a template. The primers (400 nM) were the Dys primer 2reV (5'GAG TGA ATA CAG TTT GCC CAT GGA TTG-3) and the Dys primer 8for (5'-AAG AAG TAG AGG ACT GTT ATG AAA GAG AAG-3'). The target was amplified in a RT-PCR using the following program: 50° C. for 30 min, 94° C. for 2 min followed by 10 cycles (94° C. for 10 sec, 58° C. for 30 sec, 68° C. for 1 min 10 sec) and 20 cycles (94° C. for 10 sec, 58° C. for 30 sec, 68° C. for 1 min 10 sec; +10 sec/cycle). Subsequently it was incubated for 7 min at 68° C. The reaction products of the RT-PCR were separated after stopping the reaction on a 1% agarose gel (FIG. 1).

FIG. 1 shows the amplification product of the RT-PCR having a size of 1.8 kb which was obtained using native purified AMV-RT (lane 2) and AMV-RT that was obtained by recombinant means (lane 3). Lanes 1 and 4 show a DNA molecular weight marker VI (cat. No. 1062590, Roche Molecular Biochemicals).

6.2 AMV-RT from *E. coli* LE392 pAMVαβ-4+pCHAP-5 Construct 6.2.1 Purification

*E. coli* LE392 pAMVαβ-4+pCHAP-5 cells which overexpress both chains of the AMV-RT (see above) were used as the starting material to purify the recombinant AMV-RT.

The AMV-RT was purified at 4° C. The purification was carried out by chromatographic methods after cell lysis and separation of the nucleic acids. The purification yields a recombinant AMV-RT which is free of contaminating enzyme activities and in RT-PCR has the same functionality as an AMV-RT purified from native material.

Buffer buffer A: 50 mM NaPO$_4$, pH 7.2, 1 M NaCl, 3 mM 2-mercaptoethanol, 10% glycerol, buffer B: 50 mM NaPO$_4$, pH 5.0, 1 M NaCl, 3 mM 2-mercaptoethanol, 10% glycerol, buffer C: 50 mM NaPO$_4$, pH 6.0, 1 M NaCl, 3 mM 2-mercaptoethanol, 10% glycerol, 0.2 M imidazole, buffer D: 50 mM NaPO$_4$, pH 7.7, 1 M NaCl, 3 mM 2-mercaptoethanol, 10% glycerol, 0.5 M imidazole buffer E: 50 mM NaPO$_4$, pH 6.0, 3 mM 2-mercaptoethanol, 10% glycerol, storage buffer: 200 mM potassium phosphate, pH 7.2, 2 mM DTT, 0.2% Triton X-100, 50% glycerol.

Cell Lysis

Ca. 50 g *E coli* LE392 pAMV-αβ-4+pCHAP-5 cells were mixed with 400 ml buffer A, thawed and suspended. Two tablets of Complete (Roche Molecular Biochemicals, cat. No. 1697498) were added to the suspension. Subsequently the cells were lysed by means of ultrasound (Branson sonicator) while cooling (temperature: <10° C.). The degree of lysis of the cell suspension that was achieved was typically 40–50%.

Precipitation of Nucleic Acids

Afterwards the nucleic acids were removed by means of polymin precipitation. 5 ml of a 10% polymin P solution was added dropwise. If the precipitation was incomplete, further dropwise addition was carried out. After incubation for 30 min at 4° C., centrifugation was carried out (30 min, 13000 rpm, 4° C.).

Chromatographic Purifications

Affinity chromatography on a Ni-chelate column:

The clear centrifugation supernatant was absorbed to a nickel-loaded chelating sepharose ff column (2.6 cm×10 cm, Pharmacia) which had been equilibrated with buffer A, it was then washed with ca. 500 ml buffer A, afterwards with 500 ml buffer B and 500 ml buffer C. The enzyme was eluted with buffer D in a total volume of 500 ml. The flow rate was 5 ml per minute, the fraction size was 20 ml per fraction. The pool of active fractions was dialysed against buffer E.

Chromatography on Heparin-sepharose

The dialysed pool was subsequently absorbed to a heparin-sepharose ff column (1.6 cm×10 cm, Pharmacia) equilibrated with buffer E+250 mM NaCl and washed with ca. 200 ml buffer E+250 mM NaCl. The enzyme was eluted with a linear gradient of buffer E+250 mM NaCl and buffer E+1 M NaCl in a total volume of 200 ml. The flow rate was 2.5 ml per min, the fraction size was 10 ml. The AMV-RT eluted at an NaCl concentration of 500 mM to 700 mM.

The RT-active fractions were pooled and dialysed against storage buffer. Application buffer containing SDS and β-mercaptoethanol was added to the purified protein and the sample was denatured by boiling (5 min, 100° C.). Subsequently 20 µl aliquots were analysed by an analytical SDS gel (4–20%) (Laemmli U K., 1970, Nature 227: 555–557). The α- and β-subunits of AMV-RT were found in equimolar ratios (FIG. 2, lane 6).

Figure 2:
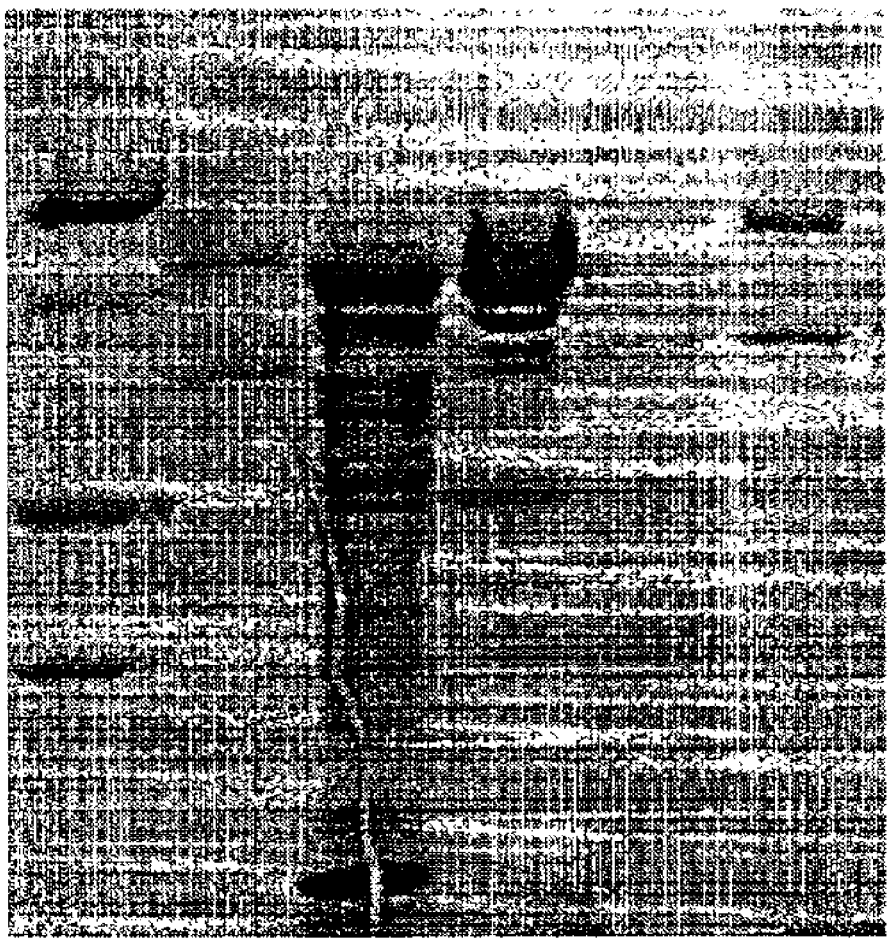
FIG. 2 shows an SDS gel with samples from the AMV-RT purification lane 1: molecular weight marker
lane 2: native AMV
lane 3: cell lysis
lane 4: Ni-chelate sepharose, wash with buffer C
lane 5: Ni-chelate pool
lane 6: rec. AMV-RT final preparation.

FIG. 2 shows an SDS gel with samples from the AMV-RT purification
lane 1: molecular weight marker
lane 2: native AMV
lane 3: cell lysis
lane 4: Ni-chelate sepharose, wash with buffer C
lane 5: Ni-chelate pool
lane 6: rec. AMV-RT final preparation The described method yields a stable AMV-RT with an equimolar distribution of the α- and β-subunits. The enzyme obtained is functional in RT-PCR.

6.2.2. Functional Test in RT-PCR

The recombinant AMV reverse transcriptase that was obtained was examined in a functional test. The functional test consists of a reverse transcription (RT), followed by a polymerase chain reaction (PCR). 10 units of the recombinant AMV reverse transcriptase was used for this. A 8 kb, 10 kb, 12 kb and a 13.5 kb fragment of the human dystrophin gene was amplified.

1 µg human muscle RNA was used as a template. The primers (400 nM) were the Dys primer 2 for (5'-CAA TCC ATG GGC AAA CTG TAT TCA CTC-3') and Dys primer 5 rev (5'-CGT CCC GTA TCA TAA ACA TTC AGC AGC-3') for 8 kb, Dys primer 8 for (5'-AAG AAG TAG AGG ACT GTT ATG AAA GAG AA-3') and 5 rev for 10 kb, Dys primer 8 for and Dys primer 9 rev (5'-AGC AGG TAA GCC TGG ATG ACT GAC TAG AAG-3') for 12 kb and Dys primer 8 for and 10 rev (5'-AAT CAA TCA ACC AAC CGA AAT CTC ACT CTG-3') for 13.5 kb. The cDNA synthesis was carried out for 60 min at 42° C.

The cDNA synthesis was carried out according to the instructions in the product information for the AMV reverse transcriptase (cat. No. 1495062, Roche Molecular Biochemicals).

Figure 3:
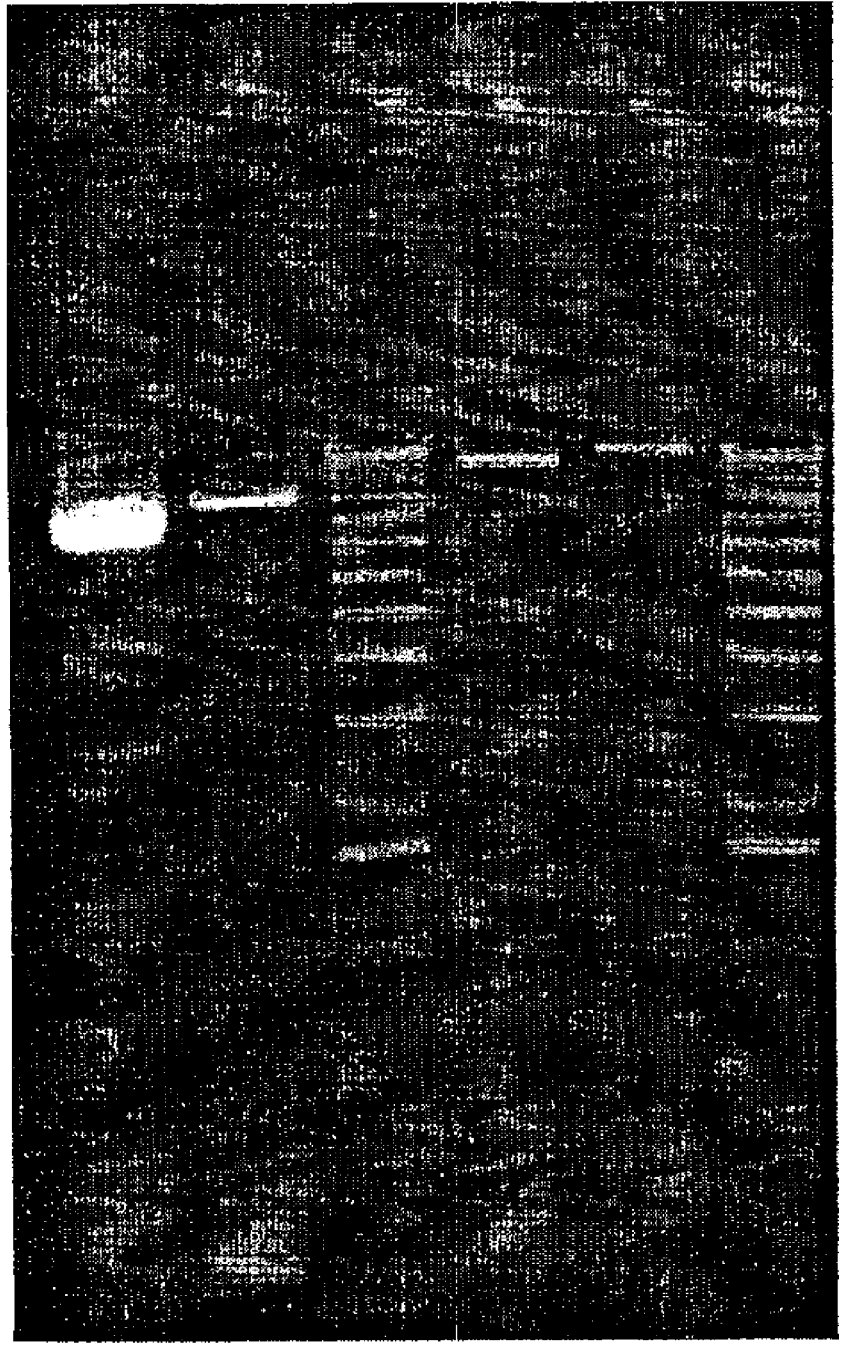
FIG. 3 shows an agarose gel on which the reaction products of the PT-PCR using recombinant AMV-RT were separated; lane 1: 8 kb amplification product, lane 2: 10 kb amplification product, lane 3: DNA length standard X, lane 4: 12 kb amplification product, lane 5: 13.5 kb amplification product, lane 6: DNA length standard X.

The Expand Long Template PCR System (cat. No. 1681834, Roche Molecular Biochemicals) was used for the PCR. The target was amplified using the following PCR program: 94° C. for 2 min, followed by 10 cycles (94° C. for 10 sec, 60° C. for 30 sec, 68° C. for 10 min) and 20 cycles (94° C. for 10 sec, 60° C. for 30 sec, 68° C. for 10 min 10+10 sec/cycle). Subsequently it was incubated for 5 min at 68° C. After stopping the reaction, the reaction products of the RT-PCR were separated on 1% agarose gel (FIG. 3). Lanes 3 and 6 show a DNA molecular weight marker X (cat. no. 1498037, Roche Molecular Biochemicals).

FIG. 3 shows an agarose gel on which the reaction products of the RT-PCR using recombinant AMV-RT were separated; lane 1: 8 kb amplification product, lane 2: 10 kb amplification product, lane 3: DNA length standard X, lane 4: 12 kb amplification product, lane 5: 13.5 kb amplification product, lane 6: DNA length standard X.

What is claimed is:

1. A method for producing an active heterodimeric avian myeloblastosis virus reverse transcriptase (AMV RT), comprising:
   (i) cloning, individually or in combination, a DNA sequence coding for an α subunit of AMV RT, a DNA sequence coding for a β subunit of AMV RT, a lacIq gene, and a dnaY gene, into one or more expression vectors,
   (ii) transforming the expression vectors into E. coli host cells,
   (iii) incubating the host cells under conditions suitable for expression of the α and β subunits of AMV RT, and
   (iv) isolating the active heterodimeric AMV RT from the cells.

2. The method of claim 1 wherein the sequence coding for the α subunit of AMV RT further codes for a peptide sequence comprising from 2 to 10 arginine residues.

3. The method of claim 1 wherein the sequence coding for the β subunit of AMV RT further codes for a peptide sequence comprising from 2 to 10 histidine residues.

4. The method of claim 1 wherein the sequence coding for the α subunit of AMV RT further codes for a peptide sequence comprising from 2 to 10 arginine residues and the sequence coding for the β subunit of AMV RT further codes for a peptide sequence comprising from 2 to 10 histidine residues.

5. The method of claim 1 wherein the DNA sequence coding for the α subunit of AMV RT comprises SEQ ID NO: 4 and the DNA sequence coding for the β subunit of AMV RT comprises SEQ ID NO: 5.

6. The method of claim 1 wherein the cloning step further comprises cloning a trpT gene coding for tryptophan tRNA into an expression vector.

7. The method of claim 1 wherein the cloning step further comprises cloning a chaperone gene selected from the group consisting of GroEL, GroES, Dnak, DnaJ, GrpE, and ClpB into an expression vector.

8. The method of claim 1 further comprising the step of purifying the isolated active heterodimeric AMV RT by means of affinity chromatography.

9. The method of claim 4 further comprising the step of purifying the isolated active heterodimeric AMV RT by means of affinity chromatography.

10. The method of claim 1 wherein the active heterodimeric AMV RT isolated from the cells is comprised of the an α subunit comprising SEQ ID NO: 6 and a β subunit comprising SEQ ID NO: 7.

* * * * *

SEQUENCE LISTING

<160> NUMBER OF SEQ ID NOS: 22

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 1
gatgactgga attcatgact gttgcgctac atctggct                                   38

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 2
gatgactgct gcagttatta tgcaaaaaga gggctcgcct                                 40

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 3
gatgactgct gcagttatta atacgcttga aaggtggctt g                               41

<210> SEQ ID NO 4
<211> LENGTH: 1716
<212> TYPE: DNA
<213> ORGANISM: Avian Myeloblastosis Virus

<400> SEQUENCE: 4

| | | | | | |
|---|---|---|---|---|---|
| actgttgcgc | tacatctggc | tattccgctc | aaatggaagc | caaaccacac | gcctgtgtgg | 60 |
| attgaccagt | ggccccttcc | tgaaggtaaa | cttgtagcgc | taacgcaatt | agtggaaaaa | 120 |
| gaattacagt | taggacatat | agaaccttca | cttagttgct | ggaacacacc | tgtctttgtg | 180 |
| atccggaagg | cttccgggtc | ttatcgctta | ttgcatgact | tgcgcgctgt | taacgctaag | 240 |
| cttgttcctt | tggggccgt | ccaacagggg | gcgccggttc | tctccgcgct | cccgcgtggc | 300 |
| tggcccctga | tggtcctaga | cctcaaggat | tgcttctttt | ctattcctct | tgcggaacaa | 360 |
| gatcgcgaag | cttttgcatt | tacgctcccc | tctgtgaata | accaggcccc | cgctcgaaga | 420 |
| ttccaatgga | aggtcttgcc | ccaagggatg | acctgttctc | ccactatctg | tcagttgata | 480 |
| gtgggtcaaa | tacttgagcc | cttgcgactc | aagcacccat | ctctgcgcat | gttgcattat | 540 |
| atggatgatc | ttttgctagc | cgcctcaagt | catgatgggt | tggaagcggc | aggggaggag | 600 |
| gttatcagta | cattggaaag | agccgggttc | accatttcgc | ctgataaggt | ccagagggag | 660 |
| cccggagtac | aatatcttgg | gtacaagtta | ggcagtacgt | atgtagcacc | cgtaggcctg | 720 |
| gtagcagaac | ccaggatagc | caccttgtgg | gatgttcaga | agctggtggg | gtcacttcag | 780 |
| tggcttcgcc | cagcgctagg | aatcccgcct | cgactgatgg | gccccttta | tgagcagtta | 840 |
| cgagggtcag | atcctaacga | ggcgagggaa | tggaatctag | acatgaaaat | ggcctggaga | 900 |
| gagatcgtgc | agctcagcac | cactgctgcc | ttggaacgat | gggaccctgc | cctgcctctg | 960 |
| gaaggagcgg | tcgctagatg | tgaacagggg | gcaatagggg | tcctgggaca | gggactgtcc | 1020 |
| acacacccaa | ggccatgttt | gtggttattc | tccacccaac | ccaccaaggc | gtttactgct | 1080 |
| tggttagaag | tgctcaccct | tttgattact | aagctacgtg | cttcggcagt | gcgaaccttt | 1140 |
| ggcaaggagg | ttgatatcct | cctgttgcct | gcatgctttc | gggaggacct | tccgctcccg | 1200 |
| gagggatcc | tgttagccct | tagggggttt | gcaggaaaaa | tcaggagtag | tgacacgcca | 1260 |
| tctattttg | acattgcgcg | tccactgcat | gtttctctga | aagtgagggt | taccgaccac | 1320 |
| cctgtaccgg | gacccactgt | ctttaccgac | gcctcctcaa | gcacccataa | ggggtggta | 1380 |
| gtctggaggg | agggcccaag | gtgggagata | aagaaatag | ctgatttggg | ggcaagtgta | 1440 |
| caacaactgg | aagcacgcgc | tgtggccatg | gcacttctgc | tgtggccgac | aacgcccact | 1500 |
| aatgtagtga | ctgactctgc | gtttgttgcg | aaaatgttac | tcaagatggg | gcaggaggga | 1560 |
| gtcccgtcta | cagcggcggc | ttttattta | gaggatgcgt | taagccaaag | gtcagccatg | 1620 |
| gccgccgttc | tccacgtgcg | gagtcattct | gaggtgccag | ggttttttcac | agaaggaaat | 1680 |
| gacgtggcag | atagccaagc | cacctttcaa | gcgtat | | | 1716 |

<210> SEQ ID NO 5
<211> LENGTH: 2574
<212> TYPE: DNA
<213> ORGANISM: Avian Myeloblastosis Virus

<400> SEQUENCE: 5

| | | | | | |
|---|---|---|---|---|---|
| actgttgcgc | tacatctggc | tattccgctc | aaatggaagc | caaaccacac | gcctgtgtgg | 60 |
| attgaccagt | ggccccttcc | tgaaggtaaa | cttgtagcgc | taacgcaatt | agtggaaaaa | 120 |

-continued

| | |
|---|---|
| gaattacagt taggacatat agaaccttca cttagttgct ggaacacacc tgtctttgtg | 180 |
| atccggaagg cttccgggtc ttatcgctta ttgcatgact tgcgcgctgt taacgctaag | 240 |
| cttgttcctt tgggccgt ccaacagggg gcgccggttc tctccgcgct cccgcgtggc | 300 |
| tggcccctga tggtcctaga cctcaaggat tgcttctttt ctattcctct tgcggaacaa | 360 |
| gatcgcgaag cttttgcatt tacgctcccc tctgtgaata accaggcccc cgctcgaaga | 420 |
| ttccaatgga aggtcttgcc ccaagggatg acctgttctc ccactatctg tcagttgata | 480 |
| gtgggtcaaa tacttgagcc cttgcgactc aagcacccat ctctgcgcat gttgcattat | 540 |
| atggatgatc ttttgctagc cgcctcaagt catgatgggt tggaagcggc aggggaggag | 600 |
| gttatcagta cattggaaag agccgggttc accatttcgc ctgataaggt ccagagggag | 660 |
| cccggagtac aatatcttgg gtacaagtta ggcagtacgt atgtagcacc cgtaggcctg | 720 |
| gtagcagaac ccaggatagc caccttgtgg gatgttcaga agctggtggg gtcacttcag | 780 |
| tggcttcgcc cagcgctagg aatcccgcct cgactgatgg gccccttta tgagcagtta | 840 |
| cgagggtcag atcctaacga ggcgagggaa tggaatctag acatgaaaat ggcctggaga | 900 |
| gagatcgtgc agctcagcac cactgctgcc ttggaacgat gggaccctgc cctgcctctg | 960 |
| gaaggagcgg tcgctagatg tgaacagggg gcaatagggg tcctgggaca gggactgtcc | 1020 |
| acacacccaa ggccatgttt gtggttattc tccacccaac ccaccaaggc gtttactgct | 1080 |
| tggttagaag tgctcaccct tttgattact aagctacgtg cttcggcagt gcgaaccttt | 1140 |
| ggcaaggagg ttgatatcct cctgttgcct gcatgctttc gggaggacct tccgctcccg | 1200 |
| gaggggatcc tgttagccct tagggggttt gcaggaaaaa tcaggagtag tgacacgcca | 1260 |
| tctattttg acattgcgcg tccactgcat gtttctctga aagtgagggt taccgaccac | 1320 |
| cctgtaccgg gacccactgt ctttaccgac gcctcctcaa gcacccataa ggggtggta | 1380 |
| gtctggaggg agggcccaag gtgggagata aagaaatag ctgatttggg ggcaagtgta | 1440 |
| caacaactgg aagcacgcgc tgtggccatg gcacttctgc tgtggccgac aacgcccact | 1500 |
| aatgtagtga ctgactctgc gtttgttgcg aaaatgttac tcaagatggg gcaggaggga | 1560 |
| gtcccgtcta cagcggcggc ttttatttta gaggatgcgt taagccaaag gtcagccatg | 1620 |
| gccgccgttc tccacgtgcg gagtcattct gaagtgccag ggtttttcac agaaggaaat | 1680 |
| gacgtggcag atagccaagc cacctttcaa gcgtatccct tgagagaggc taaagatctc | 1740 |
| cataccgctc tccatatcgg accccgcgcg ctatccaaag cgtgtaatat atctatgcag | 1800 |
| caggctaggg aggttgttca gacctgcccg cattgtaatt cagcccctgc gttggaggcc | 1860 |
| ggggtaaacc ctaggggttt ggaccccta cagatatggc agacagactt tacactagag | 1920 |
| cctagaatgg ctccccgttc ctggctcgct gttactgtgg ataccgcctc atctgcgata | 1980 |
| gtcgtaactc agcatggccg tgtcacatcg gttgctgcac aacatcattg ggccacggct | 2040 |
| atcgccgttt tgggaagacc aaaggccata aaaacagata atgggtcctg cttcacgtct | 2100 |
| aaatccacgc gagagtggct cgcgagatgg gggatagcac acaccaccgg gattccgggt | 2160 |
| aattcccagg gtcaagctat ggtagagcgg gccaaccggc tcctgaaaga taagatccgt | 2220 |
| gtgcttgcgg aggggatgg ctttatgaaa agaatcccca ccagcaaaca ggggaaacta | 2280 |
| ttagccaagg caatgtatgc ccttaatcac tttgagcgtg gtgaaaacac aaaaacaccg | 2340 |
| atacaaaaac actggagacc taccgttctt acagaaggac cccggttaa aatacgaata | 2400 |
| gagacagggt agtgggaaaa aggatggaac gtgctggtct ggggacgagg ttatgcagct | 2460 |
| gtgaaaaaca gggacactga taaggttatt tgggtaccct ctcgaaaagt taaaccggac | 2520 |

-continued atcgcccaaa aggatgaggt gactaagaaa gatgaggcga gccctctttt tgca     2574

<210> SEQ ID NO 6
<211> LENGTH: 572
<212> TYPE: PRT
<213> ORGANISM: Avian Myeloblastosis Virus

<400> SEQUENCE: 6

Thr Val Ala Leu His Leu Ala Ile Pro Leu Lys Trp Lys Pro Asn His
 1               5                  10                  15

Thr Pro Val Trp Ile Asp Gln Trp Pro Leu Pro Glu Gly Lys Leu Val
            20                  25                  30

Ala Leu Thr Gln Leu Val Glu Lys Glu Leu Gln Leu Gly His Ile Glu
        35                  40                  45

Pro Ser Leu Ser Cys Trp Asn Thr Pro Val Phe Val Ile Arg Lys Ala
    50                  55                  60

Ser Gly Ser Tyr Arg Leu Leu His Asp Leu Arg Ala Val Asn Ala Lys
65                  70                  75                  80

Leu Val Pro Phe Gly Ala Val Gln Gln Gly Ala Pro Val Leu Ser Ala
                85                  90                  95

Leu Pro Arg Gly Trp Pro Leu Met Val Leu Asp Leu Lys Asp Cys Phe
            100                 105                 110

Phe Ser Ile Pro Leu Ala Glu Gln Asp Arg Glu Ala Phe Ala Phe Thr
        115                 120                 125

Leu Pro Ser Val Asn Asn Gln Ala Pro Ala Arg Arg Phe Gln Trp Lys
    130                 135                 140

Val Leu Pro Gln Gly Met Thr Cys Ser Pro Thr Ile Cys Gln Leu Ile
145                 150                 155                 160

Val Gly Gln Ile Leu Glu Pro Leu Arg Leu Lys His Pro Ser Leu Arg
                165                 170                 175

Met Leu His Tyr Met Asp Asp Leu Leu Leu Ala Ala Ser Ser His Asp
            180                 185                 190

Gly Leu Glu Ala Ala Gly Glu Glu Val Ile Ser Thr Leu Glu Arg Ala
        195                 200                 205

Gly Phe Thr Ile Ser Pro Asp Lys Val Gln Arg Glu Pro Gly Val Gln
    210                 215                 220

Tyr Leu Gly Tyr Lys Leu Gly Ser Thr Tyr Val Ala Pro Val Gly Leu
225                 230                 235                 240

Val Ala Glu Pro Arg Ile Ala Thr Leu Trp Asp Val Gln Lys Leu Val
                245                 250                 255

Gly Ser Leu Gln Trp Leu Arg Pro Ala Leu Gly Ile Pro Pro Arg Leu
            260                 265                 270

Met Gly Pro Phe Tyr Glu Gln Leu Arg Gly Ser Asp Pro Asn Glu Ala
        275                 280                 285

Arg Glu Trp Asn Leu Asp Met Lys Met Ala Trp Arg Glu Ile Val Gln
    290                 295                 300

Leu Ser Thr Thr Ala Ala Leu Glu Arg Trp Asp Pro Ala Leu Pro Leu
305                 310                 315                 320

Glu Gly Ala Val Ala Arg Cys Glu Gln Gly Ala Ile Gly Val Leu Gly
                325                 330                 335

Gln Gly Leu Ser Thr His Pro Arg Pro Cys Leu Trp Leu Phe Ser Thr
            340                 345                 350

Gln Pro Thr Lys Ala Phe Thr Ala Trp Leu Glu Val Leu Thr Leu Leu
        355                 360                 365

```
Ile Thr Lys Leu Arg Ala Ser Ala Val Arg Thr Phe Gly Lys Glu Val
    370                 375                 380

Asp Ile Leu Leu Pro Ala Cys Phe Arg Glu Asp Leu Pro Leu Pro
385                 390                 395                 400

Glu Gly Ile Leu Leu Ala Leu Arg Gly Phe Ala Gly Lys Ile Arg Ser
                405                 410                 415

Ser Asp Thr Pro Ser Ile Phe Asp Ile Ala Arg Pro Leu His Val Ser
            420                 425                 430

Leu Lys Val Arg Val Thr Asp His Pro Val Pro Gly Pro Thr Val Phe
            435                 440                 445

Thr Asp Ala Ser Ser Ser Thr His Lys Gly Val Val Val Trp Arg Glu
450                 455                 460

Gly Pro Arg Trp Glu Ile Lys Glu Ile Ala Asp Leu Gly Ala Ser Val
465                 470                 475                 480

Gln Gln Leu Glu Ala Arg Ala Val Ala Met Ala Leu Leu Leu Trp Pro
                485                 490                 495

Thr Thr Pro Thr Asn Val Val Thr Asp Ser Ala Phe Val Ala Lys Met
            500                 505                 510

Leu Leu Lys Met Gly Gln Glu Gly Val Pro Ser Thr Ala Ala Ala Phe
            515                 520                 525

Ile Leu Glu Asp Ala Leu Ser Gln Arg Ser Ala Met Ala Ala Val Leu
530                 535                 540

His Val Arg Ser His Ser Glu Val Pro Gly Phe Phe Thr Glu Gly Asn
545                 550                 555                 560

Asp Val Ala Asp Ser Gln Ala Thr Phe Gln Ala Tyr
                565                 570

<210> SEQ ID NO 7
<211> LENGTH: 858
<212> TYPE: PRT
<213> ORGANISM: Avian Myeloblastosis Virus

<400> SEQUENCE: 7

Thr Val Ala Leu His Leu Ala Ile Pro Leu Lys Trp Lys Pro Asn His
  1               5                  10                  15

Thr Pro Val Trp Ile Asp Gln Trp Pro Leu Pro Glu Gly Lys Leu Val
             20                  25                  30

Ala Leu Thr Gln Leu Val Glu Lys Glu Leu Gln Leu Gly His Ile Glu
         35                  40                  45

Pro Ser Leu Ser Cys Trp Asn Thr Pro Val Phe Val Ile Arg Lys Ala
     50                  55                  60

Ser Gly Ser Tyr Arg Leu Leu His Asp Leu Arg Ala Val Asn Ala Lys
 65                  70                  75                  80

Leu Val Pro Phe Gly Ala Val Gln Gln Gly Ala Pro Val Leu Ser Ala
                 85                  90                  95

Leu Pro Arg Gly Trp Pro Leu Met Val Leu Asp Leu Lys Asp Cys Phe
            100                 105                 110

Phe Ser Ile Pro Leu Ala Glu Gln Asp Arg Glu Ala Phe Ala Phe Thr
        115                 120                 125

Leu Pro Ser Val Asn Asn Gln Ala Pro Ala Arg Arg Phe Gln Trp Lys
    130                 135                 140

Val Leu Pro Gln Gly Met Thr Cys Ser Pro Thr Ile Cys Gln Leu Ile
145                 150                 155                 160

Val Gly Gln Ile Leu Glu Pro Leu Arg Leu Lys His Pro Ser Leu Arg
```

-continued

```
                165                 170                 175
Met Leu His Tyr Met Asp Asp Leu Leu Ala Ala Ser Ser His Asp
                180                 185                 190

Gly Leu Glu Ala Ala Gly Glu Glu Val Ile Ser Thr Leu Glu Arg Ala
                195                 200             205

Gly Phe Thr Ile Ser Pro Asp Lys Val Gln Arg Glu Pro Gly Val Gln
                210                 215             220

Tyr Leu Gly Tyr Lys Leu Gly Ser Thr Tyr Val Ala Pro Val Gly Leu
225                         230                 235                 240

Val Ala Glu Pro Arg Ile Ala Thr Leu Trp Asp Val Gln Lys Leu Val
                    245                 250                 255

Gly Ser Leu Gln Trp Leu Arg Pro Ala Leu Gly Ile Pro Pro Arg Leu
                260                 265                 270

Met Gly Pro Phe Tyr Glu Gln Leu Arg Gly Ser Asp Pro Asn Glu Ala
                275                 280                 285

Arg Glu Trp Asn Leu Asp Met Lys Met Ala Trp Arg Glu Ile Val Gln
                290                 295                 300

Leu Ser Thr Thr Ala Ala Leu Glu Arg Trp Asp Pro Ala Leu Pro Leu
305                 310                 315                 320

Glu Gly Ala Val Ala Arg Cys Glu Gln Gly Ala Ile Gly Val Leu Gly
                    325                 330                 335

Gln Gly Leu Ser Thr His Pro Arg Pro Cys Leu Trp Leu Phe Ser Thr
                340                 345                 350

Gln Pro Thr Lys Ala Phe Thr Ala Trp Leu Glu Val Leu Thr Leu Leu
                355                 360                 365

Ile Thr Lys Leu Arg Ala Ser Ala Val Arg Thr Phe Gly Lys Glu Val
        370                 375                 380

Asp Ile Leu Leu Leu Pro Ala Cys Phe Arg Glu Asp Leu Pro Leu Pro
385                 390                 395                 400

Glu Gly Ile Leu Leu Ala Leu Arg Gly Phe Ala Gly Lys Ile Arg Ser
                    405                 410                 415

Ser Asp Thr Pro Ser Ile Phe Asp Ile Ala Arg Pro Leu His Val Ser
                420                 425                 430

Leu Lys Val Arg Val Thr Asp His Pro Val Pro Gly Pro Thr Val Phe
        435                 440                 445

Thr Asp Ala Ser Ser Ser Thr His Lys Gly Val Val Val Trp Arg Glu
        450                 455                 460

Gly Pro Arg Trp Glu Ile Lys Glu Ile Ala Asp Leu Gly Ala Ser Val
465                 470                 475                 480

Gln Gln Leu Glu Ala Arg Ala Val Ala Met Ala Leu Leu Leu Trp Pro
                    485                 490                 495

Thr Thr Pro Thr Asn Val Val Thr Asp Ser Ala Phe Val Ala Lys Met
                500                 505                 510

Leu Leu Lys Met Gly Gln Glu Gly Val Pro Ser Thr Ala Ala Ala Phe
        515                 520                 525

Ile Leu Glu Asp Ala Leu Ser Gln Arg Ser Ala Met Ala Ala Val Leu
    530                 535                 540

His Val Arg Ser His Ser Glu Val Pro Gly Phe Phe Thr Glu Gly Asn
545                 550                 555                 560

Asp Val Ala Asp Ser Gln Ala Thr Phe Gln Ala Tyr Pro Leu Arg Glu
                    565                 570                 575

Ala Lys Asp Leu His Thr Ala Leu His Ile Gly Pro Arg Ala Leu Ser
                580                 585                 590
```

```
Lys Ala Cys Asn Ile Ser Met Gln Gln Ala Arg Glu Val Val Gln Thr
            595                 600                 605
Cys Pro His Cys Asn Ser Ala Pro Ala Leu Glu Ala Gly Val Asn Pro
        610                 615                 620
Arg Gly Leu Gly Pro Leu Gln Ile Trp Gln Thr Asp Phe Thr Leu Glu
625                 630                 635                 640
Pro Arg Met Ala Pro Arg Ser Trp Leu Ala Val Thr Val Asp Thr Ala
                645                 650                 655
Ser Ser Ala Ile Val Val Thr Gln His Gly Arg Val Thr Ser Val Ala
            660                 665                 670
Ala Gln His His Trp Ala Thr Ala Ile Ala Val Leu Gly Arg Pro Lys
        675                 680                 685
Ala Ile Lys Thr Asp Asn Gly Ser Cys Phe Thr Ser Lys Ser Thr Arg
        690                 695                 700
Glu Trp Leu Ala Arg Trp Gly Ile Ala His Thr Thr Gly Ile Pro Gly
705                 710                 715                 720
Asn Ser Gln Gly Gln Ala Met Val Glu Arg Ala Asn Arg Leu Leu Lys
                725                 730                 735
Asp Lys Ile Arg Val Leu Ala Glu Gly Asp Gly Phe Met Lys Arg Ile
            740                 745                 750
Pro Thr Ser Lys Gln Gly Glu Leu Leu Ala Lys Ala Met Tyr Ala Leu
        755                 760                 765
Asn His Phe Glu Arg Gly Glu Asn Thr Lys Thr Pro Ile Gln Lys His
        770                 775                 780
Trp Arg Pro Thr Val Leu Thr Glu Gly Pro Pro Val Lys Ile Arg Ile
785                 790                 795                 800
Glu Thr Gly Glu Trp Glu Lys Gly Trp Asn Val Leu Val Trp Gly Arg
                805                 810                 815
Gly Tyr Ala Ala Val Lys Asn Arg Asp Thr Asp Lys Val Ile Trp Val
            820                 825                 830
Pro Ser Arg Lys Val Lys Pro Asp Ile Ala Gln Lys Asp Glu Val Thr
        835                 840                 845
Lys Lys Asp Glu Ala Ser Pro Leu Phe Ala
        850                 855

<210> SEQ ID NO 8
<211> LENGTH: 62
<212> TYPE: DNA
<213> ORGANISM: Artificial Sequence
<220> FEATURE:
<223> OTHER INFORMATION: Description of Artificial Sequence: Primer

<400> SEQUENCE: 8
gatgactgga attcatgcgt cgccgtcgcc gtcgccgtcg cactgttgcg ctacatctgg     60
ct                                                                    62

<210> SEQ ID NO 9
<211> LENGTH: 65
<212> TYPE: DNA
<213> ORGANISM: Artificial Sequence
<220> FEATURE:
<223> OTHER INFORMATION: Description of Artificial Sequence: Primer

<400> SEQUENCE: 9
gatgactgga attcatgaga ggcagccacc atcaccatca ccatactgtt gcgctacatc     60
tggct                                                                 65
```

<210> SEQ ID NO 10
<211> LENGTH: 425
<212> TYPE: DNA
<213> ORGANISM: Escherichia coli

<400> SEQUENCE: 10

```
ctgttttggc ggatgagaga agattttcag cctgatacag attaaatcag aacgcagaag      60
cggtctgata aaacagaatt tgcctggcgg cagtagcgcg gtggtcccac ctgaccccat     120
gccgaactca gaagtgaaac gccgtagcgc cgatggtagt gtggggtctc cccatgcgag     180
agtagggaac tgccaggcat caaataaaac gaaaggctca gtcgaaagac tgggcctttc     240
gttttatctg ttgtttgtcg gtgaacgctc tcctgagtag acaaatccg ccgggagcgg     300
atttgaacgt tgcgaagcaa cggcccggag ggtggcgggc aggacgcccg ccataaactg     360
ccaggcatca aattaagcag aaggccatgc tgacggatgg ccttttttgcg tttctacaaa     420
ctctt                                                                 425
```

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 11

```
aaaactgcag agcagtaagc cggtcataaa a                                     31
```

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 12

```
aaaactgcag cgtgctggat gaagtgtatt a                                     31
```

<210> SEQ ID NO 13
<211> LENGTH: 2155
<212> TYPE: DNA
<213> ORGANISM: Escherichia coli

<400> SEQUENCE: 13

```
atcagaattt ttttcttttt tccccttga aggggcgaag cctcatcccc atttctctgg       60
tcaccagccg ggaaaccacg taagctccgg cgtcacccat aacagatacg gactttctca    120
aaggagagtt atcaatgaat attcgtccat tgcatgatcg cgtgatcgtc aagcgtaaag    180
aagttgaaac taaatctgct ggcggcatcg ttctgaccgg ctctgcagcg gctaaatcca    240
cccgcggcga agtgctggct gtcggcaatg gccgtatcct tgaaaatggc gaagtgaagc    300
cgctggatgt gaaagttggc gacatcgtta ttttcaacga tggctacggt gtgaaatctg    360
agaagatcga caatgaagaa gtgttgatca tgtccgaaag cgacattctg gcaattgttg    420
aagcgtaatc cgcgcacgac actgaacata cgaatttaag gaataaagat aatggcagct    480
aaagacgtaa aattcggtaa cgacgctcgt gtgaaaatgc tgcgcggcgt aaacgtactg    540
gcagatgcag tgaaagttac cctcggtcca aaaggccgta acgtagttct ggataaatct    600
ttcggtgcac cgaccatcac caaagatggt gtttccgttg ctcgtgaaat cgaactggaa    660
```

```
gacaagttcg aaaatatggg tgcgcagatg gtgaaagaag ttgcctctaa agcaaacgac      720
gctgcaggcg acggtaccac cactgcaacc gtactggctc aggctatcat cactgaaggt      780
ctgaaagctg ttgctgcggg catgaacccg atggacctga acgtggtat cgacaaagcg       840 gttaccgctg cagttgaaga actgaaagcg ctgtccgtac catgctctga ctctaaagcg      900
attgctcagg ttggtaccat ctccgctaac tccgacgaaa ccgtaggtaa actgatcgct      960
gaagcgatgg acaaagtcgg taaagaaggc gttatcaccg ttgaagacgg taccggtctg     1020
caggacgaac tggacgtggt tgaaggtatg cagttcgacc gtggctacct gtctccttac     1080
ttcatcaaca agccggaaac tggcgcagta gaactgaaa gcccgttcat cctgctggct      1140
gacaagaaaa tctccaacat ccgcgaaatg ctgccggttc tggaagctgt tgccaaagca     1200
ggcaaaccgc tgctgatcat cgctgaagat gtagaaggcg aagcgctggc aactctggtt     1260
gttaacacca tgcgtggcat cgtgaaagtc gctgcggtta agcaccggg cttcggcgat      1320 cgtcgtaaag ctatgctgca ggatatcgca accctgactg gcgtaccgt gatctctgaa      1380 gagatcggta tggagctgga aaaagcaacc ctggaagacc tgggtcaggc taaacgtgtt     1440
gtgatcaaca aagacaccac cactatcatc gatggcgtgg gtgaagaagc tgcaatccag     1500
ggccgtgttg ctcagatccg tcagcagatt gaagaagcaa cttctgacta cgaccgtgaa     1560
aaactgcagg aacgcgtagc gaaactggca ggcggcgttg cagttatcaa agtgggtgct     1620
gctaccgaag ttgaaatgaa agagaaaaaa gcacgcgttg aagatgccct gcacgcgacc     1680
cgtgctgcgg tagaagaagg cgtggttgct ggtggtggtg ttgcgctgat ccgcgtagcg     1740
tctaaactgg ctgacctgcg tggtcagaac gaagaccaga acgtgggtat caaagttgca     1800
ctgcgtgcaa tggaagctcc gctgcgtcag atcgtattga actgcggcga agaaccgtct     1860
gttgttgcta acaccgttaa aggcggcgac ggcaactacg gttacaacgc agcaaccgaa     1920
gaatacggca acatgatcga catgggtatc ctggatccaa ccaaagtaac tcgttctgct     1980
ctgcagtacg cagcttctgt ggctggcctg atgatcacca ccgaatgcat ggttaccgac     2040
ctgccgaaaa acgatgcagc tgacttaggc gctgctggcg gtatgggcgg catgggtggc     2100
atgggcggca tgatgtaatt gccctgcacc tcgcagaaat aaacaaaccc ccggg          2155
```

<210> SEQ ID NO 14
<211> LENGTH: 3139
<212> TYPE: DNA
<213> ORGANISM: Escherichia coli

<400> SEQUENCE: 14

```
atgggtaaaa taattggtat cgacctgggt actaccaact cttgtgtagc gattatggat       60
ggcaccactc ctcgcgtgct ggagaacgcc gaaggcgatc gcaccacgcc ttctatcatt      120
gcctataccc aggatggtga aactctagtt ggtcagccgg ctaaacgtca ggcagtgacg      180
aacccgcaaa cactctgtt tgcgattaaa cgcctgattg gtcgccgctt ccaggacgaa       240
gaagtacagc gtgatgtttc catcatgccg ttcaaaatta ttgctgctga taacggcgac      300
gcatgggtcg aagttaaagg ccagaaaatg gcaccgccgc agatttctgc tgaagtgctg      360
aaaaaaatga agaaaaccgc tgaagattac ctgggtgaac cggtaactga agctgttatc      420
accgtaccgg catactttaa cgatgctcag cgtcaggcaa ccaaagacgc aggccgtatc      480
gctggtctgg aagtaaaacg tatcatcaac gaaccgaccg cagctgcgct ggcttacggt      540
ctggacaaag gcactggcaa ccgtactatc gcggtttatg acctgggtgg tggtactttc      600
gatatttcta ttatcgaaat cgacgaagtt gacggcgaaa aaaccttcga agttctggca      660
```

-continued

```
accaacggtg atacccacct gggggtgaa gacttcgaca gccgtctgat caactatctg    720
gttgaagaat tcaagaaaga tcagggcatt gacctgcgca acgatccgct ggcaatgcag    780
cgcctgaaag aagcggcaga aaaagcgaaa atcgaactgt cttccgctca gcagaccgac    840
gttaacctgc catacatcac tgcagacgcg accggtccga acacatgaa catcaaagtg     900
actcgtgcga aactggaaag cctggttgaa gatctggtaa accgttccat tgagccgctg    960
aaagttgcac tgcaggacgc tggcctgtcc gtatctgata tcgacgacgt tatcctcgtt   1020
ggtggtcaga ctcgtatgcc aatggttcag aagaaagttg ctgagttctt tggtaaagag   1080
ccgcgtaaag acgttaaccc ggacgaagct gtagcaatcg gtgctgctgt tcagggtggt   1140
gttctgactg gtgacgtaaa agacgtactg ctgctggacg ttaccccgct gtctctgggt   1200
atcgaaacca tgggcggtgt gatgacgacg ctgatcgcga aaacaccac tatcccgacc    1260
aagcacagcc aggtgttctc taccgctgaa gacaaccagt ctgcggtaac catccatgtg   1320
ctgcagggtg aacgtaaacg tgcggctgat aacaaatctc tgggtcagtt caacctagat   1380
ggtatcaacc cggcaccgcg cggcatgccg cagatcgaag ttaccttcga tatcgatgct   1440
gacggtatcc tgcacgtttc cgcgaaagat aaaaacagcg gtaaagagca aagatcacc    1500
atcaaggctt cttctggtct gaacgaagat gaaatccaga aaatggtacg cgacgcagaa   1560
gctaacgccg aagctgaccg taagtttgaa gagctggtac agactcgcaa ccagggcgac   1620
catctgctgc acagcacccg taagcaggtt gaagaagcag gcgacaaaact gccggctgac   1680
gacaaaactg ctatcgagtc tgcgctgact gcactggaaa ctgctctgaa aggtgaagac   1740
aaagccgcta tcgaagcgaa aatgcaggaa ctggcacagg tttcccagaa actgatggaa   1800
atcgcccagc agcaacatgc ccagcagcag actgccggtg ctgatgcttc tgcaaacaac   1860
gcgaaagatg acgatgttgt cgacgctgaa tttgaagaag tcaaagacaa aaaataatcg   1920
ccctataaac gggtaattat actgacacgg gcgaagggga atttcctctc cgcccgtgca   1980
ttcatctagg ggcaatttaa aaaagatggc taagcaagat tattacgaga ttttaggcgt   2040
ttccaaaaca gcggaagagc gtgaaatcag aaaggcctac aaacgcctgg ccatgaaata   2100
ccacccggac cgtaaccagg gtgacaaaga ggccgaggcg aaatttaaag agatcaagga   2160
agcttatgaa gttctgaccg actcgcaaaa acgtgcggca tacgatcagt atggtcatgc   2220
tgcgtttgag caaggtggca tgggcggcgg cggttttggc ggcggcgcag acttcagcga   2280
tatttttggt gacgtttttcg gcgatattt tggcggcgga cgtggtcgtc aacgtgcggc   2340
gcgcggtgct gatttacgct ataacatgga gctcaccctc gaagaagctg tacgtggcgt   2400
gaccaaagag atccgcattc cgactctgga agagtgtgac gttttgccacg gtagcggtgc   2460
aaaaccaggt acacagccgc agacttgtcc gacctgtcat ggttctggtc aggtgcagat   2520
gcgccaggga ttcttcgctg tacagcagac ctgtccacac tgtcagggcc gcggtacgct   2580
gatcaaagat ccgtgcaaca atgtcatgg tcatggtcgt gttgagcgca gcaaaacgct   2640
gtccgttaaa atcccggcag gggtggacac tggagaccgc atccgtcttg cgggcgaagg   2700
tgaagcgggc gagcatggcg caccggcagg cgatctgtac gttcaggttc aggttaaaca   2760
gcacccgatt ttcgagcgtg aaggcaacaa cctgtattgc gaagtcccga tcaacttcgc   2820
tatggcggcg ctgggtggcg aaatcgaagt accgaccctt gatggtcgcg tcaaactgaa   2880
agtgcctggc gaaacccaga ccggtaagct attccgtatg cgcggtaaag gcgtcaagtc   2940
tgtccgcggt ggcgcacagg gtgatttgct gtgccgcgtt gtcgtcgaaa caccggtagg   3000
```

-continued

```
cctgaacgaa aggcagaaac agctgctgca agagctgcaa gaaagcttcg gtggcccaac    3060
cggcgagcac aacagcccgc gctcaaagag cttctttgat ggtgtgaaga agttttttga    3120
cgacctgacc cgctaataa                                                 3139
```

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 15

```
cccccccggg atgggtaaaa taattggtat cgac                                34
```

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 16

```
cgcgggatcc ttattagcgg gtcaggtcgt caaaaaa                             37
```

<210> SEQ ID NO 17
<211> LENGTH: 594
<212> TYPE: DNA
<213> ORGANISM: Escherichia coli

<400> SEQUENCE: 17

```
atgagtagta aagaacagaa aacgcctgag gggcaagccc cggaagaaat tatcatggat     60
cagcacgaag agattgaggc agttgagcca gaagcttctg ctgagcaggt ggatccgcgc    120
gatgaaaaag ttgcgaatct cgaagctcag ctggctgaag cccagacccg tgaacgtgac    180
ggcattttgc gtgtaaaagc cgaaatggaa aacctgcgtc gtcgtactga actggatatt    240
gaaaaagccc acaaattcgc gctggagaaa ttcatcaacg aattgctgcc ggtgattgat    300
agcctggatc gtgcgctgga agtggctgat aaagctaacc cggatatgtc tgcgatggtt    360
gaaggcattg agctgacgct gaagtcgatg ctggatgttg tgcgtaagtt tggcgttgaa    420
gtgatcgccg aaactaacgt cccactggac ccgaatgtgc atcaggccat cgcaatggtg    480
gaatctgatg acgttgcgcc aggtaacgta ctgggcatta tgcagaaggg ttatacgctg    540
aatggtcgta cgattcgtgc ggcgatggtt actgtagcga aagcaaaagc ttaa          594
```

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 18

```
cgcggaattc atgagtagta aagaacagaa aacg                                34
```

<210> SEQ ID NO 19
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 19

-continued

```
aaaactgcag ttattaagct tttgctttcg ctacagt                                37
```

<210> SEQ ID NO 20
<211> LENGTH: 2574
<212> TYPE: DNA
<213> ORGANISM: Escherichia coli

<400> SEQUENCE: 20

```
atgcgtctgg atcgtcttac taataaattc cagcttgctc ttgccgatgc ccaatcactt        60
gcactcgggc acgacaacca atttatcgaa ccacttcatt taatgagcgc cctgctgaat       120
caggaagggg gttcggttag tcctttatta acatccgctg cataaatgc tggccagttg        180
cgcacagata tcaatcaggc attaaatcgt ttaccgcagg ttgaaggtac tggtggtgat       240
gtccagccat acaggatct ggtgcgcgtt cttaatcttt gcgacaagct ggcgcaaaaa        300
cgtggtgata actttatctc gtcagaactg ttcgttctgg cggcacttga gtctcgcggc       360
acgctggccg acatcctgaa agcagcaggg gcgaccaccg ccaacattac tcaagcgatt       420
gaacaaatgc gtggaggtga aagcgtgaac gatcaaggtg ctgaagacca acgtcaggct       480
ttgaaaaaat ataccatcga ccttaccgaa cgagccgaac agggcaaact cgatccggtg       540
attggtcgtg atgaagaaat cgccgtacc attcaggtgc tgcaacgtcg tactaaaaat        600
aacccggtac tgattggtga acccggcgtc ggtaaaactg ccatcgttga aggtctggcg       660
cagcgtatta tcaacggcga agtgccggaa gggttgaaag ccgccgggt actggcgctg       720
gatatgggcg cgctggtggc tggggcgaaa tatcgcggtg agtttgaaga acgttttaaa       780
ggcgtgctta cgatcttgc caaacaggaa ggcaacgtca tcctattat cgacgaatta       840
cataccatgt tcggcgcggg taaagccgat ggcgcaatgg acgccggaaa catgctgaaa       900
ccggcgctgg cgcgtggtga attgcactgc gtaggtgcca cgacgcttga cgaatatcgc       960
cagtacattg aaaaagatgc tgcgctggaa cgtcgtttcc agaaagtgtt tgttgccgag      1020
ccttctgttg aagataccat tgcgattctg cgtggcctga agaacgttta cgaattgcac      1080
caccatgtgc aaattactga cccggcaatt gttgcagcgg cgacgttgtc tcatcgctac      1140
attgctgacc gtcagctgcc ggataaagcc atcgacctga tcgatgaagc agcatccagc      1200
attcgtatgc agattgactc aaaaccagaa gaactcgacc gactcgatcg tcgtatcatc      1260
cagctcaaac tggaacaaca ggcgttaatg aaagagtctg atgaagccag taaaaaacgt      1320
ctggatatgc tcaacgaaga actgagcgac aagaacgtc agtactccga gttagaagaa      1380
gagtggaaag cagagaaggc atcgctttct ggtacgcaga ccattaaagc ggaactggaa      1440
caggcgaaaa tcgctattga acaggctcgc cgtgtggggg acctggcgcg gatgtctgaa      1500
ctgcaatacg gcaaaatccc ggaactggaa aagcaactgg aagccgcaac gcagctcgaa      1560
ggcaaaacta tgcgtctgtt gcgtaataaa gtgaccgacg ccgaaattgc tgaagtgctg      1620
gcgcgttgga cggggattcc ggtttctcgc atgatggaaa gcgagcgcga aaaactgctg      1680
cgtatggagc aagaactgca ccatcgcgta attggtcaga acgaagcggt tgatgcggta      1740
tctaacgcta ttcgtcgtag ccgtgcgggg ctggcggatc aaatcgcccg attggttca       1800
ttcctgttcc tcggcccaac tggtgtgggg aaaacagagc tttgtaaggc gctggcgaac      1860
tttatgtttg atagcgacga ggcgatggtc cgtatcgata tgtccgagtt tatggagaaa      1920
cactcggtgt ctcgtttggt tggtgcgcct ccgggatatg tcggttatga agaaggtggc      1980
tacctgaccg aagcggtgcg tcgtcgtccg tattccgtca tcctgctgga tgaagtggaa      2040
```

-continued

```
aaagcgcatc cggatgtctt caacattctg ttgcaggtac tggatgatgg gcgtctgact    2100
gacgggcaag ggagaacggt cgacttccgt aatacggtcg tcattatgac ctctaacctc    2160
ggttccgatc tgattcagga acgcttcggt gaactggatt atgcgcacat gaaagagctg    2220
gtgctcggtg tggtaagcca taacttccgt ccggaattca ttaaccgtat cgatgaagtg    2280
gtggtcttcc atccgctggg tgaacagcac attgcctcga ttgcgcagat tcagttgaaa    2340
cgtctgtaca aacgtctgga agaacgtggt tatgaaatcc acatttctga cgaggcgctg    2400
aaactgctga gcgagaacgg ttacgatccg gtctatggtg cacgtcctct gaaacgtgca    2460
attcagcagc agatcgaaaa cccgctggca cagcaaatac tgtctggtga attggttccg    2520
ggtaaagtga ttcgcctgga agttaatgaa gaccggattg tcgccgtcca gtaa          2574
```

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 21
aaaactgcag atgcgtctgg atcgtcttac taat                                 34

<210> SEQ ID NO 22
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 22
cccgggaagc ttattactgg acggcgacaa tccggtc                              37